(12) United States Patent
Heckel et al.

(10) Patent No.: US 6,169,106 B1
(45) Date of Patent: Jan. 2, 2001

(54) INDOLINONES HAVING KINASE INHIBITORY ACTIVITY

(75) Inventors: Armin Heckel; Rainer Walter; Wolfgang Grell, all of Biberach; Jacobus C. A. van Meel, Mittelbiberach; Norbert Redemann, Biberach, all of (DE)

(73) Assignee: Boehringer Ingelheim Pharma KG, Ingelheim (DE)

( * ) Notice: Under 35 U.S.C. 154(b), the term of this patent shall be extended for 0 days.

(21) Appl. No.: 09/286,983

(22) Filed: Apr. 6, 1999

Related U.S. Application Data

(60) Provisional application No. 60/090,227, filed on Jun. 22, 1998.

(30) Foreign Application Priority Data

Apr. 15, 1998 (DE) ............................................. 198 16 624

(51) Int. Cl.[7] ........................ A61K 31/404; C07D 209/04
(52) U.S. Cl. ........................ 514/415; 514/418; 514/414; 548/452; 548/468
(58) Field of Search ..................... 514/414, 415, 514/418; 548/452, 468; 544/452, 468

(56) References Cited

FOREIGN PATENT DOCUMENTS

788890 * 8/1997 (EP) .

97/13767 * 4/1997 (WO) .

* cited by examiner

Primary Examiner—Mukund J. Shah
Assistant Examiner—Sudhaker B. Patel
(74) Attorney, Agent, or Firm—R. P. Raymond; M-E M. Devlin; A. R. Stempel

(57) ABSTRACT

The present invention relates to substituted indolinones of general formula

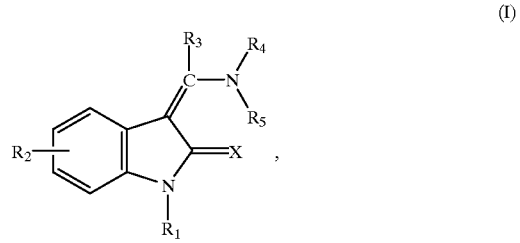

(I)

wherein $R_1$ to $R_5$, and X are defined as in claim 1, the isomers thereof and the salts thereof, particularly the physiologically acceptable salts thereof which have valuable pharmacological properties, particularly an inhibitory effect on various kinases and cycline/CDK complexes and on the proliferation of various tumour cells, pharmaceutical compositions containing these (compounds, their use and processes for preparing them.

7 Claims, No Drawings

INDOLINONES HAVING KINASE INHIBITORY ACTIVITY

RELATED APPLICATIONS

The benefit of prior provisional application Ser. No. 60/090,227, filed on Jun. 22, 1998, is hereby claimed.

DESCRIPTION OF THE INVENTION

The present invention relates to new substituted indolinones of general formula

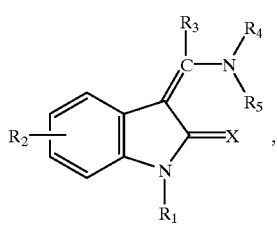

(I)

the isomers thereof, the salts thereof, particularly the physiologically acceptable salts thereof which have valuable properties.

The above compounds of general formula I wherein $R_1$, denotes a hydrogen atom or a prodrug group have valuable pharmacological properties, particularly an inhibiting effect on various kinases, especially complexes of CDKs (CDK1, CDK2, CDK3, CDK4, CDK6, CDK7, CDK8 and CDK9) with their specific cyclines (A, B1, B2, C, D1, D2, D3, E, F, G1, G2, H, I and K) and on viral cycline (cf. L. Mengtao in J. Virology 71(3), 1984–1991 (1997)), and the other compounds of the above general formula I wherein R1 does not represent a hydrogen atom or a prodrug group are valuable intermediate products for preparing the abovementioned compounds.

Thus, the present invention relates to the above compounds of general formula I (the compounds wherein R1 denotes a hydrogen atom or A prodrug group having valuable pharmacological properties), the pharmaceutical compositions containing the pharmacologically active compounds, their use and processes for preparing them.

In the above general formula I

X denotes an oxygen or sulphur atom, $R_1$ denotes a hydrogen atom, a $C_{1-4}$-alkoxy-carbonyl or $C_{2-4}$-alkanoyl group, $R_2$ denotes a carboxy-, $C_{1-4}$-alkoxy-carbonyl or aminocarbonyl group wherein the amino moiety may be substituted by one or two $C_{1-3}$-alkyl groups and the substituents may be identical or different, $R_3$ denotes a phenyl or naphthyl group which may be substituted by fluorine, chlorine or bromine atoms, by $C_{1-3}$-alkyl, $C_{1-3}$-alkoxy, cyano, trifluoromethyl, nitro, amino, $C_{1-3}$-alkylamino, di-($C_{1-3}$-alkyl)-amino, $C_{2-4}$-alkanoyl-amino, N-($C_{1-3}$-alkyl)-$C_{2-4}$-alkanoylamino, N-($C_{1-3}$-alkyl)-$C_{2-4}$-alkanoylamino, $C_{1-3}$-alkylsulphonylamino, amino-$C_{1-3}$-alkyl, $C_{1-3}$-alkylamino-$C_{1-3}$-alkyl, di-($C_{1-3}$-alkyl)-amino-$C_{1-3}$-alkyl, N-($C_{2-4}$-alkanoyl)-amino-$C_{1-3}$-alkyl or N-($C_{2-4}$-alkanoyl)-$C_{1-3}$-alkylamino-$C_{1-3}$-alkyl groups and the substituents may be identical or different, $R_4$ denotes a hydrogen atom or a $C_{1-3}$-alkyl group and $R_5$ denotes a hydrogen atom, a $C_{1-5}$-alkyl group optionally substituted by a phenyl, carboxy or $C_{1-3}$-alkoxy-carbonyl group, a $C_{3-7}$-cycloalkyl group optionally substituted by a $C_{1-3}$-alkyl group, an indanyl group optionally substituted by a $C_{1-3}$-aikyl group, a 5-membered heteroaryl group which contains an imino group optionally substituted by a $C_{1-3}$-alkyl group, an oxygen or sulphur atom or an imino group optionally substituted by a $C_{1-3}$-alkyl group and an oxygen, sulphur or nitrogen atom or two nitrogen atoms or a 6-membered heteroaryl group which contains 1 to 3 nitrogen atoms, whilst additionally a 1,3-butadienylene bridge may be attached via two adjacent carbon atoms or via one carbon atom and an adjacent imino group of the abovementioned 5- and 6-membered heteroaryl groups and the carbon skeleton of the abovementioned mono- and bicyclic rings may be mono or disubstituted by fluorine, chlorine, bromine or iodine atoms, by $C_{1-5}$-alkyl or cyano groups and the substituents may be identical or different, a pyrrolidinyl or piperidinyl group linked via a carbon atom, which may be substituted at the nitrogen atom by a $C_{1-3}$-alkyl group, a phenyl group optionally disubstituted by fluorine, chlorine, bromine or iodine atoms, by $C_{1-5}$-alkyl, $C_{1-3}$-alkoxy, carboxy, $C_{1-3}$-alkoxycarbonyl, aminosulphonyl, nitro or cyano groups, whilst the substituents may be identical or different, a phenyl, pyridyl, pyrimidyl or thienyl group each of which is substituted by a trifluoromethoxy group, by a fluorine, chlorine, bromine or iodine atom, by a $C_{1-3}$-alkoxy group which may be substituted in the 2- or 3-position by an amino, $C_{1-3}$-alkylamino, di-($C_{1-3}$-alkyl) amino, phenyl-$C_{1-3}$-alkylamino, N-($C_{1-3}$-alkyl)-phenyl-$C_{1-3}$-alkylamino, pyrrolidino or piperidino group, by a phenyl-$C_{1-3}$-alkylamino-$C_{1-3}$-alkyl group which may be mono- or disubstituted in the phenyl nucleus by a trifluoromethyl group, by fluorine, chlorine, bromine or iodine atoms, by $C_{1-5}$-alkyl or $C_{1-3}$-alkoxy groups, whilst the substituents may be identical or different, and additionally may be replaced at the amine nitrogen atom by a $C_{1-3}$-alkyl group wherein the hydrogen atoms from position 2 may be wholly or partially replaced by fluorine atoms, by a $C_{1-5}$-alkyl, phenyl, imidazolyl, $C_{3-7}$-cycloalkyl, $C_{1-3}$-alkoxy-$C_{1-3}$-alkoxy, phenyl-$C_{1-3}$-alkoxy, carboxy-$C_{1-3}$-alkyl, $C_{1-3}$-alkoxycarbonyl-$C_{1-3}$-alkyl, carboxy, $C_{1-3}$-alkoxycarbonyl, aminocarbonyl, $C_{1-3}$-alkylaminocarbonyl, di-($C_{1-3}$-alkyl)-aminocarbonyl, phenyl-$C_{1-3}$-alkylaminocarbonyl, N-($C_{1-3}$-alkyl)-phenyl-$C_{1-3}$-alkylaminocarbonyl, piperazinocarbonyl, N-($C_{1-3}$-alkyl)-piperazinocarbonyl, nitro, amino, $C_{1-3}$-alkylamino, di-($C_{1-3}$-alkyl)-amino, pyrrolidino, piperidino, morpholino, $C_{2-4}$-alkanoyl-amino, N-($C_{1-3}$-alkyl)-$C_{2-4}$-alkanoylamino, benzoylamino or N-($C_{1-3}$-alkyl)-benzoylamino group, by an N-($C_{1-3}$-alkyl)-$C_{2-4}$-alkanoylamino group which is additionally substituted in the alkyl moiety by a carboxy or $C_{1-3}$-alko)xycarbonyl group, by a $C_{1-3}$-alkylaminocarbonyl or di-($C_{1-3}$-alkyl)-aminocarbonyl group wherein an alkyl moiety is additionally substituted by a di-($C_{1-3}$-alkyl)-amino group, or by an N-($C_{1-3}$-alkyl)-$C_{1-3}$-alkylsulphonylamino or N-($C_{1-3}$-alkyl)-phenylsulphonylamino group wherein the alkyl moiety may additionally be substituted by a cyano, carboxy, $C_{1-3}$-alkoxycarbonyl, $C_{1-3}$-alkylamino, di-($C_{1-3}$-alkyl)-amino group, eminocarbonyl, $C_{1-3}$-alkylaminocarbonyl, di-($C_{1-3}$-alkyl)-aminocarbonyl, piperidinocarbonyl or 2-[di-($C_{1-3}$-alkylamino)]-ethylaminocarbonyl group, a phenyl or thienyl group substituted by a $C_{1-3}$-alkyl group wherein the alkyl moiety is substituted by a hydroxy, $C_{1-3}$-alkoxy, carboxy, $C_{1-3}$-alkoxy-carbonyl, amino, $C_{1-5}$alkylamino, di-($C_{1-5}$-alkyl)-amino, $C_{2-4}$-alkanoylamino, N-($C_{1-3}$-alkyl)-$C_{2-4}$-alkanoylamino, pyrrolidino, dehydropyrrolidino, piperidino, dehydropiperidino, 3-hydroxypiperidino, 4-hydroxypiperidino, hexamethyleneimino, morpholino, thiomorpholino, piperazino, 4-($C_{1-3}$-alkyl)-piperazino, 4-phenyl-piperazino, 4-($C_{2-4}$-alkanoyl)-piperazino, 4-benzoyl-piperazino or imidazolyl group, whilst the abovementioned saturated cycloalkyleneimino rings, $C_{1-5}$-alkylamino or di-($C_{1-5}$-alkyl)-amino groups may additionally be substituted by one or two $C_{1-5}$-alkyl groups, by a $C_{3-7}$-cycloalkyl, hydroxy, $C_{1-3}$-alkoxy, carboxy, $C_{1-3}$-alkoxycarbonyl, aminocarbonyl, $C_{1-3}$-alkylaminocarbonyl or di-($C_{1-3}$-alkyl)-aminocarbonyl group, by a phenyl-$C_{1-3}$-alkyl or phenyl group optionally mono- or disubstituted in the phenyl nucleus by fluorine, chlorine, bromine or iodine atoms or by $C_{1-3}$-alkyl or cyano groups, whilst the substituents may be identical or different, or a methylene group adjacent to the nitrogen atom in the abovementioned cycloalkyleneimino rings may be replaced by a carbonyl or sulphonyl group, and the abovementioned monosubstituted phenyl groups may additionally be substituted by a fluorine, chlorine or bromine atom or by a methyl, amino, $C_{1-3}$-alkylamino or di-($C_{1-3}$-alkyl-amino group, or a phenyl ring optionally substituted by one or two $C_{1-3}$-alkoxy groups may be fused to one of the abovementioned unsubstituted cycloalkyleneimino rings via two adjacent carbon atoms.

The carboxy groups mentioned in the definition of the groups above may also be replaced by a group which can be converted in vivo into a carboxy group and the amino and imino groups mentioned in the definition of the groups above may also be replaced by a group which can be cleaved in vivo.

Moreover, the saturated alkyl and alkoxy moieties mentioned in the above definition containing more than 2 carbon atoms also include the branched isomers thereof, such as, for example, the isopropyl, tert.butyl, isobutyl group, etc.

Preferred compounds of general formula I are those wherein

X denotes an oxygen or sulphur atom, $R_1$ denotes a hydrogen atom, a $C_{1-4}$-alkoxy-carbonyl or $C_{2-4}$-alkanoyl group, $R_2$ denotes a carboxy-, $C_{1-4}$-alkoxy-carbonyl or aminocarbonyl group wherein the amino moiety may be substituted by one or two $C_{1-3}$-alkyl groups and the substituents may be identical or different, $R_3$ denotes a phenyl or naphthyl group which may be substituted by fluorine, chlorine or bromine atoms, by $C_{1-3}$-alkyl, $C_{1-3}$-alkoxy, cyano, trifluoromethyl, nitro, amino, $C_{1-3}$-alkylamino, di-($C_{1-3}$-alkyl)-amino, $C_{2-4}$-alkanoyl-amino, N-($C_{1-3}$-alkyl)-$C_{2-4}$-alkanoylamino, N-($C_{1-3}$-alkyl)-$C_{2-4}$-alkanoylamino, $C_{1-3}$-alkylsulphonylamino, amino-$C_{1-3}$-alkyl, $C_{1-3}$-alkylamino-$C_{1-3}$-alkyl, di-($C_{1-3}$-alkyl)-amino-$C_{1-3}$-alkyl, N-($C_{2-4}$-alkanoyl)-amino-$C_{1-3}$-alkyl or N-($C_{2-4}$-alkanoyl)-$C_{1-3}$-alkylamino-$C_{1-3}$-alkyl groups and the substituents may be identical or different, $R_4$ denotes a hydrogen atom or a $C_{1-3}$-alkyl group and $R_5$ denotes a hydrogen atom, a $C_{1-5}$-a-kyl group optionally substituted by a phenyl, carboxy or $C_{1-3}$-alkoxy-carbonyl group, a $C_{3-7}$-cycloalkyl group optionally substituted by a $C_{1-3}$-alkyl group, an indanyl group optionally substituted by a $C_{1-3}$-alkyl group, a 5-membered heteroaryl group which contains an imino group optionally substituted by a $C_{1-3}$-alkyl group, an oxygen or sulphur atom or an imino group optionally substituted by a $C_{1-3}$-alkyl group and an oxygen, sulphur or nitrogen atom or two nitrogen atoms or a 6-membered heteroaryl group which contains 1 to 3 nitrogen atoms, whilst additionally a 1,3-butadienylene bridge may be attached via two adjacent carbon atoms or via one carbon atom and an adjacent imino group of the abovementioned 5- and 6-membered heteroaryl groups and the carbon skeleton of the abovementioned mono- and bicyclic rings may be mono or disubstituted by fluorine, chlorine, bromine or iodine atoms, by $C_{1-5}$-alkyl or cyano groups and the substituents may be identical or different, a pyrrolidinyl or piperidinyl group linked via a carbon atom, which may be substituted at the nitrogen atom by a $C_{1-3}$-alkyl group, a phenyl group optionally mono- or disubstituted by fluorine, chlorine, bromine or iodine atoms, by $C_{1-5}$-alkyl or cyano groups, whilst the substituents may be identical or different, a phenyl, pyridyl, pyrimidyl or thienyl group each of which is substituted by a $C_{3-7}$-cycloalkyl, $C_{1-3}$-alkoxy, phenyl-$C_{1-3}$-alkoxy, carboxy-$C_{1-3}$-alkyl, $C_{1-3}$-alkoxycarbonyl-$C_{1-3}$-alkyl, carboxy, $C_{1-3}$-alkoxycarbonyl, aminocarbonyl, $C_{1-3}$-alkylamino-carbonyl, di-($C_{1-3}$-alkyl)-aminocarbonyl, nitro, amino, $C_{1-3}$-alkylamino, di-($C_{1-3}$-alkyl)-amino, $C_{2-4}$-alkanoyl-amino, N-($C_{1-3}$-alkyl)-$C_{2-4}$-alkanoylamino or N-($C_{1-3}$-alkyl)-$C_{2-4}$-alka-noylamino group, by a $C_{1-3}$-alkylaminocarbonyl group wherein the alkyl moiety additionally substituted by a di-($C_{1-3}$-alkyl)-amino group, or by a N-($C_{1-3}$-alkyl)-$C_{1-3}$-alkylsulphonylamino group wherein the alkyl moiety may additionally be substituted by a cyano, carboxy, $C_{1-3}$-alkoxycarbonyl, $C_{1-3}$-alkylamino or di-($C_{1-3}$-alkyl)-amino group, a phenyl or thienyl group substituted by a $C_{1-3}$-alkyl group wherein the alkyl moiety is substituted by a hydroxy, $C_{1-3}$-alkoxy, carboxy, $C_{1-3}$-alkoxy-carbonyl, amino, $C_{1-5}$-alkylamino, di-($C_{1-5}$-alkyl)-amino, $C_{2-4}$-alkanoylamino, N-($C_{1-3}$-alkyl)-$C_{2-4}$-alkanoylamino, pyrrolidinc, piperidino, hexamethyleneimino, morpholino, piperazino, 4-($C_{1-3}$-alkyl)-piperazino, 4-($C_{2-4}$-alkanoyl)-piperazino, 4-benzoyl-piperazino or imidazolyl group, whilst the abovementioned cycloalkyleneimino rings, $C_{1-5}$-alkylamino or di-($C_{1-5}$-alkyl)-amino groups may additionally be substituted by a $C_{1-5}$-alkyl, $C_{3-7}$-cycloalkyl, hydroxy, $C_{1-3}$-alkoxy, carboxy, $C_{1-3}$-alk-oxycarbonyl, aminocarbonyl, $C_{1-3}$-alkylaminocarbonyl or di-($C_{1-3}$-alkyl)-aminocarbonyl group, by a phenyl-$C_{1-3}$-alkyl or phenyl group optionally mono or disubstituted in the phenyl nucleus by fluorine, chlorine, bromine or iodine atoms or by $C_{1-3}$-alkyl or cyano groups, whilst the substituents may be identical or different, or a methylene group adjacent to the nitrogen atom in the abovementioned cycloalkyleneimino rings may be replaced by a carbonyl or sulphonyl group, and the abovementioned monosubstituted phenyl group may additionally be substituted by a fluorine, chlorine or bromine atom or by a methyl group, particularly those compounds of general formula I wherein X denotes an oxygen atom, $R_1$ denotes a hydrogen atom or a $C_{1-4}$-alkoxycarbonyl group, $R_2$ denotes a carboxy, $C_{1-4}$-alkoxycarbonyl or aminocarbonyl group wherein the amino moiety may be substituted by one or two $C_{1-3}$-alkyl groups and the substituents may be identical or different, $R_3$ denotes a phenyl group optionally substituted by a fluorine, chlorine or bromine atom, by a methyl, cyano or aminomethyl group, $R_4$ denotes a hydrogen atom or a methyl group and $R_5$ denotes a hydrogen atom, a $C_{1-5}$-alkyl group optionally substituted by a carboxy or $C_{1-3}$-alkoxycarbonyl group, or a benzyl group, a $C_{3-7}$-cycloalkyl group optionally substituted by a methyl group, an indanyl, pyridyl, oxazolyl, thiazolyl or imidazolyl group optionally substituted by a methyl group, to which a phenyl ring may additionally be fused via two adjacent carbon atoms, a methylphenyl group optionally substituted by a fluorine, chlorine or bromine atom, or by a methoxy, carboxy, $C_{1-3}$-alkyloxycarbonyl, nitro or aminosulphonyl group, or a dimethoxyphenyl group, a pyrrolidinyl or piperidinyl group linked via a carbon atom, which may be substituted at the nitrogen atom by a $C_{1-3}$-alkyl group, a phenyl group which is substituted by a trifluoromethoxy group, by a fluorine, chlorine, bromine or iodine atom, by a $C_{1-3}$-alkoxy group which may be substituted in the 2- or 3- position by an amino, $C_{1-3}$-alkylamino, di-($C_{1-3}$-alkyl) amino, phenyl-$C_{1-3}$-alkylamino, N-($C_{1-3}$-alkyl)-phenyl-$C_{1-3}$-alkylamino, pyrrolidino or piperidino group, by a phenyl-$C_{1-3}$-alkylamino-$C_{1-3}$-alkyl group which may be [substituted] in the phenyl nucleus by a fluorine, chlorine, bromine or iodine atom, by a $C_{1-5}$-alkyl, $C_{1-3}$-alkoxy or trifluoromethyl group and additionally at the amine nitrogen atom by a $C_{1-3}$-alkyl group wherein the hydrogen atoms from position 2 may be wholly or partially replaced by fluorine atoms, by a $C_{1-5}$-alkyl, phenyl, imidazolyl, $C_{3-7}$-cycloalkyl, $C_{1-3}$-alkoxy-$C_{1-3}$-alkoxy, phenyl-$C_{1-3}$-alkoxy, carboxy-$C_{1-3}$-alkyl, $C_{1-3}$-alkoxycarbonyl-$C_{1-3}$-alkyl, carboxy, $C_{1-3}$-alkoxycarbonyl, aminocarbonyl, $C_{1-3}$-alkylaminocarbonyl, di-($C_{1-3}$-alkyl)-aminocarbonyl, phenyl-$C_{1-3}$-alkylaminocarbonyl, N-($C_{1-3}$-alkyl)-phenyl-$C_{1-3}$-alkylaminocarbonyl, piperazinocarbonyl, N-($C_{1-3}$-alkyl)-piperazinocarbonyl, nitro, amino, $C_{1-3}$-alkylamino, di-($C_{1-3}$-alkyl)-amino, pyrrolidino, piperidino, morpholino, $C_{2-4}$-alkanoyl-amino, N-($C_{1-3}$-alkyl)-$C_{2-4}$-alkanoylamino, benzoylamino or N-($C_{1-3}$-alkyl)-benzoylamino group, by an N-($C_{1-3}$-alkyl)-$C_{2-4}$-alkanoylamino group which is additionally substituted in the alkyl moiety by a carboxy or $C_{1-3}$-alkoxycarbonyl group, by a $C_{1-3}$-alkylaminocarbonyl or di-($C_{1-3}$-alkyl)-aminocarbonyl group wherein an alkyl moiety is additionally substituted by a di-($C_{1-3}$-alkyl)-amino group, or by an N-($C_{1-3}$-alkyl)-$C_{1-3}$-alkylsulphonylamino or N-($C_{1-3}$-alkyl)-phenylsulphonylamino group wherein the alkyl moiety may additionally be substituted by a cyano, carboxy, $C_{1-3}$-alkoxycarbonyl, $C_{1-3}$-alkylamino, di- ($C_{1-3}$-alkyl)-amino group, aminocarbonyl, $C_{1-3}$-alkylaminocarbonyl, di-($C_{1-3}$-alkyl)-aminocarbonyl, piperidinocarbonyl or 2-[di-($C_{1-3}$-alkylamino)]-ethylaminocarbonyl group, a phenyl group optionally substituted by a $C_{1-3}$-alkyl group wherein the alkyl moiety is substituted by a hydroxy, $C_{1-3}$-alkoxy, carboxy, $C_{1-3}$-alkoxy-carbonyl, amino, $C_{1-5}$-alkylamino, di-($C_{1-5}$-alkyl)-amino, $C_{2-4}$-alkanoylamino, N-($C_{1-3}$-alkyl)-$C_{2-4}$-alkanoylamino, pyrrolidino, dehydropyrrolidino, piperidino, dehydropiperidino, 3-hydroxypiperidino, 4-hydroxypiperidino, hexamethyleneimino, morpholino, thiomorpholino, piperazino, 4-($C_{1-3}$-alkyl)-piperazino, 4-phenyl-piperazino, 4-($C_{2-4}$-alkanoyl)-piperazino, 4-benzoyl-piperazino or imidazolyl group, whilst the abovementioned saturated cycloalkyleneimino rings, $C_{1-5}$-alkylamino or di-($C_{1-5}$-alkyl)-amino groups may additionally be substituted by one or two $C_{1-5}$-alkyl groups, by a $C_{3-7}$-cycloalkyl, hydroxy, $C_{1-3}$-alkoxy, carboxy, $C_{1-3}$-alk-oxycarbonyl, aminocarbonyl, $C_{1-3}$-alkylaminocarbonyl or di-($C_{1-3}$-alkyl)-aminocarbonyl group, by a phenyl-$C_{1-3}$-alkyl or phenyl group optionally mono- or disubstituted in the phenyl nucleus by fluorine, chlorine, bromine or iodine atoms or by $C_{1-3}$-alkyl or cyano groups, whilst the substituents may be identical or different, or a methylene group adjacent to the nitrogen atom in the abovementioned cycloalkyleneimino rings may be replaced by a carbonyl or sulphonyl group, and the abovementioned monosubstituted phenyl groups may additionally be substituted by a fluorine, chlorine or bromine atom or by a methyl, amino, $C_{1-3}$-alkylamino or di-($C_{1-3}$-alkyl)-amino group, or a phenyl ring optionally substituted by one or two $C_{1-3}$-alkoxy groups may be fused to one of the above-mentioned unsubstituted cycloalkyleneimino rings via two adjacent carbon atoms, the isomers and salts thereof.

Particularly preferred compounds of the above general formula I are those wherein X denotes an oxygen atom, $R_1$ denotes a hydrogen atom, $R_2$ denotes a carboxy, $C_{1-4}$-alkoxycarbonyl or aminocarbonyl group wherein the amino moiety may be substituted by one or two $C_{1-3}$-alkyl groups and the substituents may be identical or different, $R_3$ denotes a phenyl group optionally substituted by a methyl group, $R_4$ denotes a hydrogen atom or a methyl group and $R_5$ denotes a hydrogen atom, a $C_{1-3}$-alkyl group, a benzyl group or a methyl or ethyl group substituted by a carboxy or $C_{1-3}$-alkoxycarbonyl group, a $C_{3-7}$-cycloalkyl group optionally substituted by a methyl group, an indanyl, pyridyl, oxazolyl, thiazolyl or imidazolyl group optionally substituted by a methyl group, to which a phenyl ring may additionally be fused via two adjacent carbon atoms, a methylphenyl group optionally substituted by a fluorine, chlorine or bromine atom, or by a methoxy, carboxy, $C_{1-3}$-alkyloxycarbonyl, nitro or aminosulphonyl group, or a dimethoxyphenyl group, a 3-pyrrolidinyl or 4-piperidinyl group which may be substituted at the nitrogen atom by a $C_{1-3}$-alkyl group, a phenyl group which is substituted by a trifluoromethoxy, benzyloxy, cyano or nitro group, by a fluorine, chlorine or bromine atom, by a $C_{1-3}$-alkoxy group, whilst the ethoxy and n-propoxy groups may each be terminally substituted by a dimethylamino, diethylamino, N-ethyl-methylamino, N-benzyl-methylamino or piperidino group, by a phenyl-$C_{1-3}$-alkylamino-$C_{1-3}$-alkyl group which may be substituted in the phenyl nucleus by a fluorine, chlorine, bromine or iodine atom, by a methyl, methoxy or trifluoromethyl group and additionally at the amine nitrogen atom by a $C_{1-5}$-alkyl or 2,2,2-trifluoroethyl group, by a $C_{1-4}$-alkyl, phenyl, imidazolyl, cyclohexyl, methoxymethyl, carboxymethyl, $C_{1-3}$-alkoxycarbonyl-methyl, carboxy, $C_{1-3}$-alkoxycarbonyl, aminocarbonyl, $C_{1-3}$-alkylamino-carbonyl, di-($C_{1-3}$-alkyl)-aminocarbonyl, phenyl-$C_{1-3}$-alkylaminocarbonyl, N-($C_{1-3}$-alkyl)-phenyl-$C_{1-3}$-alkylaminocarbonyl, piperazinocarbonyl, N-($C_{1-3}$-alkyl)-piperazinocarbonyl, amino, $C_{1-3}$-alkylamino, di-($C_{1-3}$-alkyl)-amino, pyrrolidino, piperidino, morpholino, $C_{2-4}$-alkanoyl-amino, N-($C_{1-3}$-alkyl)-$C_{2-4}$-alkanoylamino, benzoylamino or N-($C_{1-3}$-alkyl)-benzoylamino group, by an N-($C_{1-3}$-alkyl)-$C_{2-4}$-alkanoylamino group which is additionally substituted in the alkyl moiety by a carboxy or $C_{1-3}$-alkoxycarbonyl group, by a $C_{1-3}$-alkylaminocarbonyl or di-($C_{1-3}$-alkyl)-aminocarbonyl group wherein an alkyl moiety is additionally substituted by a di-($C_{1-3}$-alkyl)-amino group, or by an N-($C_{1-3}$-alkyl)-$C_{1-3}$-alkylsulphonylamino or N-($C_{1-3}$-alkyl)-phenylsulphonylamino group wherein the alkyl moiety may additionally be substituted by a cyano, carboxy, $C_{1-3}$-alkoxycarbonyl, $C_{1-3}$-alkylamino, di-($C_{1-3}$-alkyl)-amino group, aminocarbonyl, $C_{1-3}$-alkylaminocarbonyl, di-($C_{1-3}$-alkyl)-aminocarbonyl, piperidinocarbonyl or 2-[di-($C_{1-3}$-alkylamino)]-ethylaminocarbonyl group, a phenyl group optionally substituted by a $C_{1-3}$-alkyl group wherein the alkyl moiety is substituted by a hydroxy, $C_{1-3}$-alkoxy, carboxy, $C_{1-3}$-alkoxy-carbonyl, amino, $C_{1-5}$-alkylamino, di-($C_{1-5}$-alkyl)-amino, $C_{2-4}$-alkanoylamino, N-($C_{1-3}$-alkyl)-$C_{2-4}$-alkanoylamino, pyrrolidino, dehydropyrrolidino, piperidino, dehydropiperidino, 4-hydroxypiperidino, hexamethyleneimino, morpholino, thiomorpholino, piperazino, 4-($C_{1-3}$-alkyl)-piperazino, 4-phenyl-piperazino, 4-($C_{2-4}$-alkanoyl)-piperazino, 4-benzoyl-piperazino or imidazolyl group, whilst the abovementioned saturated cycloalkyleneimino rings may additionally be substituted by a phenyl group or by one or two methyl groups, the abovementioned $C_{1-5}$-alkylamino and di-($C_{1-5}$-alkyl)-amino groups may additionally be substituted by one or two $C_{1-3}$-alkyl groups, by a cyclohexyl, hydroxy, $C_{1-3}$-alkoxy, carboxy, $C_{1-3}$-alkoxycarbonyl, aminocarbonyl, $C_{1-3}$-alkylaminocarbonyl or di-($C_{1-3}$-alkyl)-aminocarbonyl group, by a phenyl-$C_{1-3}$-alkyl or phenyl group optionally substituted in the phenyl nucleus by a fluorine, chlorine, bromine or iodine atom or by a methyl or cyano group, or a methylene group adjacent to the nitrogen atom in the abovementioned cycloalkyleneimino rings may be replaced by a carbonyl or sulphonyl group, and the abovementioned monosubstituted phenyl groups may additionally be substituted by a fluorine, chlorine or bromine atom or by a methyl, amino, $C_{1-3}$-alkylamino or di-($C_{1-3}$-alkyl)-amino group, or a phenyl ring optionally substituted by one or two $C_{1-3}$-alk,Dxy groups may be fused to one of the abovementioned unsubstituted cycloalkyleneimino rings via two adjacent carbon atoms, the isomers and salts thereof.

Most particularly preferred compounds of the above general formula I are those wherein X denotes an oxygen atom, $R_1$ denotes a hydrogen atom, $R_2$ denotes a carboxy or aminocarbonyl group wherein the amino moiety may be substituted by one or two $C_{1-3}$-alkyl groups and the substituents may be identical or different, $R_3$ denotes a phenyl group optionally substituted by a methyl group, $R_4$ denotes a hydrogen atom and $R_5$ denotes a hydrogen atom, a 3-pyrrolidinyl or 4-piperidinyl group which may be substituted at the nitrogen atom by a $C_{1-3}$-alkyl group, a phenyl group which is substituted by a $C_{1-3}$-alkoxy group, whilst the ethoxy and n-propoxy groups may each be terminally substituted by a dimethylamino, diethylamino, N-ethyl-methylamino, N-benzyl-methylamino or piperidino group, by a phenyl-$C_{1-3}$-alkylamino-$C_{1-3}$-alkyl group which may be substituted in the phenyl nucleus by a fluorine, chlorine, bromine or iodine atom, by a methyl, methoxy or trifluoromethyl group and additionally at the amine nitrogen atom by a $C_{1-5}$-alkyl or 2,2,2-trifluoroethyl group, a phenyl group optionally substituted by a $C_{1-3}$-alkyl group wherein the alkyl moiety is substituted by a hydroxy, $C_{1-3}$-alkoxy, carboxy, $C_{1-3}$-alkoxy-carbonyl, amino, $C_{1-5}$-alkylamino, di-($C_{1-5}$-alkyl)-amino, $C_{2-4}$-alkanoylamino, N-($C_{1-3}$-alkyl)-$C_{2-4}$-alkanoylamino, pyrrolidino, dehydropyrrolidino, piperidino, dehydropiperidino, 4-hydroxypiperidino, hexamethyleneimino, morpholino, thiomorpholino, piperazino, 4-($C_{1-3}$-alkyl)-piperazino, 4-phenyl-piperazino, 4-($C_{2-4}$-alkanoyl)-piperazino, 4-benzoyl-piperazino or imidazolyl group, whilst the abovementioned saturated cycloalkyleneimino rings may additionally be substituted by a phenyl group or by one or two methyl groups, the abovementioned $C_{1-5}$-alkylamino and di-($C_{1-5}$-alkyl)-amino groups may additionally be substituted by one or two $C_{1-3}$-alkyl groups, by a cyclohexyl, hydroxy, $C_{1-3}$-alkoxy, carboxy, $C_{1-3}$-alkoxycarbonyl, aminocarbonyl, $C_{1-3}$-alkylaminocarbonyl or di-($C_{1-3}$-alkyl)-aminocarbonyl group, by a phenyl-$C_{1-3}$-alkyl or phenyl group optionally substituted in the phenyl nucleus by a fluorine, chlorine, bromine or iodine atom or by a methyl or cyano group, or a methylene group adjacent to the nitrogen atom in the abovementioned cycloalkyleneimino rings may be replaced by a carbonyl or sulphonyl group, and the abovementioned monosubstituted phenyl groups may additionally be substituted by a fluorine, chlorine or bromine atom or by a methyl, amino, $C_{1-3}$-alkvlamino or di-($C_{1-3}$-alkyl)-amino group, or a phenyl ring optionally substituted by one or two $C_{1-3}$-alkoxy groups may be fused to one of the abovementioned unsubstituted cycloalkyleneimino rings via two adjacent carbon atoms, the isomers and salts thereof.

Particularly preferred are the abovementioned compounds wherein the group $R_2$ is in the 5-position, particularly the following compounds:

(a) 3-Z-[1-(4-aminomethyl-phenylamino)-1-phenyl-methylene]-5-amido-2-indolinone, (b) 3-Z-(1-phenylamino)-1-phenyl-methylene)-5-amido-2-indolinone, (c) 3-Z-[1-(4-bromophenylamino)-1-phenyl-methylene]-5-amido-2-indolinone, (d) 3-Z-[1-(4-dimethylamino-methyl)-phenylamino)-1-phenyl-methylene]-5-amido-2-indolinone, (e) 3-Z-[1-(4-pyrrolidinomethyl-phenylamino)-1-phenyl-methylene]-5-amido-2-indolinone, (f) 3-Z-[1-(4-piperidinomethyl-phenylamino)-1-phenyl-methylene]-5-amido-2-indolinone, (g) 3-Z-[1-(4-hexamethyleneiminomethyl-phenylamino)-1-phenyl-methylene]-5-amido-2-indolinone, (h) 3-Z-[1-(4-(4-benzyl-piperidino)-methyl)-phenylamino)-1-phenyl-methylene]-5-amido-2-indolinone, (i) 3-Z-[1-(4-(N-butyl-aminomethyl)-phenylamino)-1-phenyl-methylene]-5-amido-2-indolinone, (j) 3-Z-[1-(4-(N-(phenyl-methyl)-aminomethyl)-phenylamino)-1-phenyl-methylene]-5-amido-2-indolinone, (k) 3-Z-[1-(4-(N-methyl-N-benzyl-amino-methyl)-phenylamino)-1-phenyl-methylene]-5-amido-2-indolinone, (l) 3-Z-[1-(4-piperidino-methyl-phenylamino)-1-phenyl-methylene]-5-dimethylcarbamoyl-2-indolinone, (m) 3-Z-[1-(4-piperidino-methyl-phenylamino)-1-phenyl-methylene]-5-diethylcarbamoyi-2-indolinone, (n) 3-Z-[1-(4-(3-diethylamino-propoxy)-phenylamino)-1-phenyl-methylene]-5-amido-2-indolinone and the salts thereof.

According to the invention the new compounds are obtained for example using the following methods known in principle from the literature:

a. reacting a compound of general formula

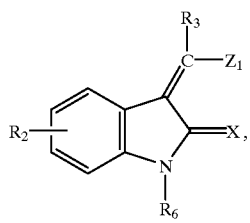

(II)

wherein

X, $R_2$ and $R_3$ are as hereinbefore defined, $R_6$ denotes a hydrogen atom, a protecting group for the nitrogen atom of the lactam group or a bond to a solid phase and $Z_1$ denotes a halogen atom, a hydroxy, alkoxy or aralkoxy group, e.g. a chlorine or bromine atom, a methoxy, ethoxy or benzyloxy group, with an amine of general formula

(III)

wherein $R_4$ and $R_5$ are as hereinbefore defined, and if necessary subsequently cleaving any protecting group used for the nitrogen atom of the lactam group, or cleaving from a solid phase.

A suitable protecting group for the nitrogen atom of the lactam group might be for example an acetyl, benzoyl, ethoxycarbonyl, tert.butyloxycarbonyl or benzyloxycarbonyl group and a suitable solid phase might be a Rink or Sieber resin.

The reaction is conveniently carried out in a solvent such as dimethylformamide, toluene, acetonitrile, tetrahydrofuran, dimethylsulphoxide, methylene chloride or mixtures thereof, optionally in the presence of an inert base such as triethylamine, N-ethyl-diisopropylamine or sodium hydrogen carbonate at temperatures between 20° and 175° C., whilst any protecting group used can be cleaved simultaneously by transamidation.

If $Z_1$ in a compound of general formula II denotes a halogen atom, the reaction is preferably carried out in the presence of an inert base at temperatures between 20° and 120° C.

If $Z_1$ in a compound of general formula II denotes a hydroxy, alkoxy or aralkoxy group, the reaction is preferably carried out at temperatures between 20° and 200° C.

If any protecting group used subsequently has to be cleaved, this is conveniently carried out either hydrolytically in an aqueous or alcoholic solvent, e.g. in methanol/water, ethanol/water, isopropanol/water, tetrahydrofuran/water, dioxane/water, dimethylformamide/water, methanol or ethanol in the presence of an alkali metal base such as lithium hydroxide, sodium hydroxide or potassium hydroxide at temperatures between 0° and 1000° C., preferably at temperatures between 10° and 500° C., or advantageously by transamidation with a primary or secondary organic base such as ammonia, methylamine, butylamine, dimethylamine or piperidine in a solvent such as methanol, ethanol, dimethylformamide and mixtures thereof or in an excess of the amine used at temperatures between 0° and 100° C., preferably at temperatures between 10° and 50° C.

Any solid phase used is preferably cleaved using trifluoroacetic acid and water in the presence of a dialkyleulphide such as dimethylsulphide at temperatures between 0° and 35° C., preferably at ambient temperature.

b. In order to prepare a compound of general formula I which contains an aminomethyl group and X denotes an oxygen atom:

Reduction of a compound of general formula

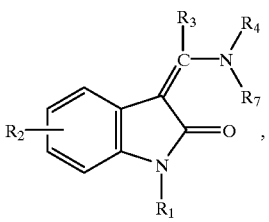

(IV)

wherein $R_1$ to $R_4$ are as hereinbefore defined and $R_7$ has the meanings given for $R_5$ hereinbefore with the proviso that $R_5$ contains a cyano group.

The reduction is preferably carried out by catalytic hydrogenation with hydrogen in the presence of a catalyst such as palladium/charcoal or platinum in a solvent such as methanol, ethanol, ethyl acetate, dimethylformamide, dimethylformamide/acetone or glacial acetic acid optionally with the addition of an acid such as hydrochloric acid at temperatures between 0° and 50° C., but preferably at ambient temperature, and at a hydrogen pressure from 1 to 7 bar, but preferably from 3 to 5 bar.

If according to the invention a compound of general formula I is obtained which contains an alkoxycarbonyl group, this can be converted by hydrolysis into a corresponding carboxy compound, or If a compound of general formula I is obtained which contains an amino or alkylamino group, this may be converted by alkylation or reductive alkylation into a corresponding alkylamino or dialkylamino compound, or If a compound of general formula I is obtained which contains an amino or alkylamino group, this may be converted by acylation into a corresponding acyl compound, or If a compound of general formula I is obtained which contains a carboxy group, this can be converted by esterification or amidation into a corresponding ester or aminocarbonyl compound.

The subsequent hydrolysis is preferably carried out in an aqueous solvent, e.g. in water, isopropanol/water, tetrahydrofuran/water or dioxane/water, in the presence of an acid such as trifluoroacetic acid, hydrochloric acid or sulphuric acid or in the presence of an alkali metal base such as lithium hydroxide, sodium hydroxide or potassium hydroxide at temperatures between 0° and 100° C., preferably at temperatures between 10° and 50° C.

The subsequent reductive alkylation is preferably carried out in a suitable solvent such as methanol, methanol/water, methano-l/water/ammonia, ethanol, ether, tetrahydrofuran, dioxane or dimethylformamide optionally with the addition of an acid such as hydrochloric acid in the presence of catalytically activated hydrogen, e.g. hydrogen in the presence of Raney nickel, platinum or palladium/charcoal, or in the presence of a metal hydride such as sodium borohydride, lithium borohydride or lithium aluminium hydride at temperatures between 0° and 100° C., preferably at temperatures between 20° and 80° C.

The subsequent alkylation is carried out with an alkylating agent such as an alkyl halide or dialkyl sulphate such as methyliodide, dimethylsulphate or propylbromide preferably in a solvent such as methanol, ethanol, methylene chloride, tetrahydrofuran, toluene, dioxane, dimethylsuilphoxide or dimethylformamide optionally in the presence of an inorganic or a tertiary organic base such as triethylamine, N-ethyl-diisopropylamine or dimethylaminopyridine, preferably at temperatures between 20° C. and the boiling temperature of the solvent used.

The subsequent acylation is preferably carried out in a solvent such as methylene chloride, diethylether, tetrahydrofuran, toluene, dioxane, acetonitrile, dimethylsulphoxide or dimethylformamide, optionally in the presence of an inorganic or a tertiary organic base, preferably at temperatures between 20° C. and the boiling temperature of the solvent used. The acylation with a corresponding acid is preferably carried out in the presence of a dehydrating agent, e.g. in the presence of isobutyl chloroformate, tetraethyl orthocarbonate, trimethyl orthoacetate, 2,2-dimethoxypropane, tetramethoxysilane, thionylchloride, trimethylchlorosilane, phosphorus trichloride, phosphorus pentoxide, N,N'-dicyclohexylcarbo-diimide, N,N'-dicyclohexyl-carbodiimide/N-hydroxysuccinimide, N,N'-dicyclohexylcarbodiimide/1-hydroxy-benztriazole, 2-(1H-benzotriazol-1-y1)-1,1,3,3-tetramethyluronium-tetrafluoroborate, 2-(1H-benzotriazol-1-y1)-1,1,3,3-tetramethyluronium-tetrafluoroborate/1-hydroxy-benzotriazole, N,N'-carbonyldiimidazole or triphenylphosphine/carbon tetrachloride, and optionally with the addition of a base such as pyridine, 4-dimethylamino-pyridine, N-methyl-morpholine or triethylamine, conveniently at temperatures between 0° and 150° C., preferably at temperatures between 0° and 100° C., and the acylation with a corresponding reactive compound such as an anhydride, ester, imidazolide or halide thereof is optionally carried out in the presence of a tertiary organic base such as triethylamine, N-ethyl-diisopropylamine or N-methyl-morpholine at temperatures between 0 and 150° C., preferably at temperatures between 50 and 100° C.

The subsequent esterification or amidation is conveniently carried out by reacting a corresponding reactive carboxylic acid derivative with a corresponding alcohol or amine as described hereinbefore.

In the reactions described hereinbefore, any reactive groups present such as carboxy, amino, alkylamino or imino groups may be protected during the reaction by conventional protecting groups which are cleaved again after the reaction.

For example, a protecting group for a carboxyl group may be a trimethylsilyl, methyl, ethyl, tert.butyl, benzyl or tetrahydropyranyl group and protecting groups for an amino, alkylamino or imino group may be an acetyl, trifluoroacetyl, benzoyl, ethoxycarbonyl, tert.butoxycarbonyl, benzyloxycarbonyl, benzyl, methoxybenzyl or 2,4-dimethoxybenzyl group and additionally, for the amino group, a phthalyl group.

Any protecting group used is optionally subsequently cleaved for example by hydrolysis in an aqueous solvent, e.g. in water, isopropanol/water, acetic acid/water, tetrahydrofuran/water or dioxane/water, in the presence of an acid such as trifluoroacetic acid, hydrochloric acid or sulphuric acid or in the presence of an alkali metal base such as lithium hydroxide, sodium hydroxide or potassium hydroxide, at temperatures between 0 and 100° C., preferably at temperatures between 10 and 50° C.

However, a benzyl, methoxybenzyl or benzyloxycarbonyl group is cleaved, for example, hydrogenolytically, e.g. with hydrogen in the presence of a catalyst such as palladium/charcoal in a solvent such as methanol, ethanol, ethyl acetate, dimethylformamide, dimethylformamide/acetone or glacial acetic acid, optionally with the addition of an acid such as hydrochloric acid or glacial acetic acid at temperatures between 0 and 50° C., but preferably at ambient temperature, and at a hydrogen pressure of 1 to 7 bar, but preferably 3 to 5 bar.

A methoxybenzyl group may also be cleaved in the presence of an oxidising agent such as cerium (IV) ammonium nitrate in a solvent such as methylene chloride, acetonitrile or acetonitrile/water at temperatures of between 0 and 50° C., but preferably at ambient temperature.

A 2,4-dimethoxybenzyl group, however, is preferably cleaved in trifluoroacetic acid in the presence of anisol.

A tert.butyl or tert.butyloxycarbonyl group is preferably cleaved by treating with an acid such as trifluoroacetic acid or hydrochloric acid, optionally using a solvent such as methylene chloride, dioxan, ethyl acetate or ether.

A phthalyl group is preferably cleaved in the presence of hydrazine or a primary amine such as methylamine, ethylamine or n-butylamine in a solvent such as methanol, ethanol, isopropanol, toluene/water or dioxan at temperatures between 20 and 50° C.

Moreover, chiral compounds of general formula I obtained may be resolved into their enantiomers and/or diastereomers.

Thus, for example, the compounds of general formula I obtained which occur as racemates may be separated by methods known per se (cf. Allinger N. L. and Eliel E. L. in "Topics in Stereochemistry", Vol. 6, Wiley Interscience, 1971) into their optical antipodes and compounds of general formula I with at least 2 asymmetric carbon atoms may be resolved into their diastercomers on the basis of their physical-chemical differences using methods known per se, e.g. by chromatography and/or fractional crystallisation, and, if these compounds are obtained in racemic form, they may subsequently be resolved into the enantiomers as mentioned above.

The enantiomers are preferably separated by column separation on chiral phases or by recrystallisation from an optically active solvent or by reacting with an optically active substance which forms salts or derivatives such as e.g. esters or amides with the racemic compound, particularly acids and the activated derivatives or alcohols thereof, and separating the diastereomeric mixture of salts or derivatives thus obtained, e.g. on the basis of their differences in solubility, whilst the free antipodes may be released from the pure diastereomeric salts or derivatives by the action of suitable agents. Optically active acids in common use are e.g. the D- and L-forms of tartaric acid or dibenzoyltartaric acid, di-o-tolyltartaric acid, malic acid, mandelic acid, camphorsulphonic acid, glutamic acid, N-acetylglutamic acid, aspartic acid, N-acetylaspartic acid or quinic acid. An optically active alcohol may be for example (+) or (−)-menthol and an optically active acyl group in amides, for example, may be a (+)-or (−)-menthyloxycarbonyl group.

Furthermore, the compounds of formula I obtained may be converted into the salts thereof, particularly for pharmaceutical use into the physiologically acceptable salts with inorganic or organic acids. Acids which may be used for this purpose include for example hydrochloric acid, hydrobromic acid, sulphuric acid, phosphoric acid, fumaric acid, succinic acid, lactic acid, citric acid, tartaric acid, maleic acid or methanesulphonic acid.

Moreover, if the new compounds of formula I thus obtained contain a carboxy group, they may subsequently, if desired, be converted into the salts thereof with inorganic or organic bases, particularly for pharmaceutical use into the physiologically acceptable salts thereof. Suitable bases for this purpose include for example sodium hydroxide, potassium hydroxide, cyclohexylamine, ethanolamine, diethanolamine and triethanolamine.

The compounds of general formulae I to VIII used as starting materials are known from the literature in some cases or may be obtained by methods known from the literature or are described in the Examples.

As already mentioned, the new compounds of general formula I wherein R1 represents a hydrogen atom or a prodrug group have valuable pharmacological properties, particularly inhibitory effects on various kinases and cycline/CDK-complexes, on the proliferation of cultivated human tumour cells and, when administered orally, on the growth of tumours in nude mice infected with human tumour cells.

For example, the compounds listed in Table 1 were tested for their biological properties as follows:

TEST 1

Inhibition of Cycline/CDK Enzyme, in Vitro Activity

High Five™ insect cells (BTI-TN-5B$_{1-4}$) which had been infected with a high titre of recombinant baculovirus were used to produce active human cycline/CDK holoenzymes. By using a baculovirus vector which contained two promoters (polyhedrin enhancer promoter, P10 enhancer promoter), GST-tagged cyclines (e.g. cycline D1 or cycline D3) with the corresponding His6-tagged CDK subunit (e.g. for CDK4 or CDK6) were expressed in the same cell. The active holoenzyme was isolated by affinity chromatography on glutathione sepharose.

Recombinant GST-tagged pRB (aa 379–928) was produced in E. coli and purified by affinity chromatography on glutathione sepharose.

The substrates used for the kinase assays depended on the specific kinases. Histone H1 (Sigma) was used as the substrate for cycline E/CDK2, cycline A/CDK2, cycline B/CDK1 and for v-cycline/CDK6. GST-tagged pRB (aa 379–928) was used as substrate for cycline D1/CDK4, cycline D3/CDK4, cycline D1/CDK6 and for cycline D3/CDK6.

Lysates of the insect cells infected with recombinant baculovirus or recombinant kinases (obtained from the lysates by purification) were incubated together with radiolabelled ATP in the presence of a suitable substrate with various concentrations of the inhibitor in a 1% DMSC) solution (dimethyl sulphoxide) for 45 minutes at 30° C. The substrate proteins with associated radioactivity were precipitated with 5% TCA (trichloroacetic acid) in water-repellent PVDF multi-well microtitre plates (Millipore) or with 0.5% phosphoric acid solution on Whatman P81 filters. After the addition of scintillation liquid the radioactivity was measured in a Wallace 1450 Microbeta Liquid Scintillation Counter. For each concentration of the substance double measurements were carried out; IC50 values were calculated for the enzyme inhibition.

TEST 2

Inhibition of the Proliferation of Cultivation Human Tumour Cells

Cells cf the Leimyosarcoma tumour cell line SK-UT-1B (obtained from the American Type Culture Collection (ATCC)) were cultivated in Minimum Essential Medium with non-essential amino acids (Gibco), supplemented with sodium pyruvate (1 mmol), glutamine (2 mmol) and 10% foetal calf serum (Gibco) and harvested during the log-growth phase. Then the SK-UT-1B cells were added to Cytostar® multi-well plates (Amersham) at a density of 4000 cells per well and incubated overnight in an incubator. Various concentrations of the compounds (dissolved in DMSO; final concentration: <1%) were added to the cells. After 48 hours' incubation 14C-thymidine (Amersham) was added to each well and incubation was continued for a further 24 hours. The quantity of 14C-thymidine incorporated into the tumour cells in the presence of the inhibitor and representing the number of cells in the S phase was measured in a Wallace 1450 Microbeta Liquid Scintillation Counter. IC50 values for the inhibition of proliferation (=inhibition of incorporated 14C-thymidine) were calculated, correcting for the background radiation. All the measurements were done twice.

TEST 3

In Vivo Effects on Tumour-Bearing Nude Mice 106 cells [SK-UT-1B, or non-small cell lung tumour NCI-H460 (obtained from ATCC)] in a volume of 0.1 ml were injected subcutaneously into male and/or female nude mice (NMRI nu/nu; 25–35 g; N=10–20); alternatively, small fragments of SK-UT-1B or NCI-H460 cell clumps were implanted subcutaneously. One to three weeks after the injection or implantation a kinase inhibitor was administered daily by oral route for a period of 2 to 4 weeks (by oesophageal tube). The size of the tumour was measured three times a week using a digital sliding gauge.

The effect of a kinase inhibitor on the tumour growth was determined as a percentage inhibition compared with a control group treated with placebo.

Table 2 which follows contains the results obtained in in vitro test 2:

| Compound (Example no.) | Inhibition of SKUT-1B- proliferation IC$_{50}$ [□m] |
|---|---|
| 4 (2) | 0.17 |
| 4 (14) | 0.18 |
| 4 (62) | 0.05 |
| 4 (53) | 0.01 |
| 4 (54) | 0.03 |
| 4 (60) | 0.03 |
| 4 (120) | 0.04 |
| 4 (122) | 0.04 |
| 4 (94) | 0.03 |
| 3 (3) | 0.01 |
| 3 (7) | 0.01 |
| 4 (129) | 0.04 |

In view of their biological properties, the new compounds of general formula I, their isomers and physiologically acceptable salts are suitable for the treatment of diseases characterised by excessive or abnormal cell proliferation.

Such diseases include (with no claim to completeness): viral infections (e.g. HIV and Kaposi's sarcoma); inflammation and autoimmune diseases (e.g. colitis, arthritis, Alzheimer's disease, glomerulonephritis and wound healing); bacterial, fungal and/or parasitic infections; leukaemias, lymphoma and solid tumours; skin diseases (e.g. psoriasis); bone diseases; cardiovascular diseases (e.g. restenosis and hypertrophy). They are also useful for protecting proliferating cells (e.g. hair, intestinal, blood and progenitor cells) against DNA damage caused by radiation, UV treatment and/or cytostatic treatment.

The new compounds may be used for the short-term or long-term treatment of the abovementioned diseases, optionally in conjunction with other state-of-the-art compounds such as other cytostatics.

The dosage required to achieve such an effect is appropriately 0.1 to 30 mg/kg, preferably 0.3 to 10 mg/kg by intravenous route, and 0.1 to 100 mg/kg, preferably 0.3 to 30 mg/kg by oral route, in each case administered 1 to 4 times a day. For this purpose, the compounds of formula I prepared according to the invention may be formulated, optionally together with other active substances, with one or more inert conventional carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethyleneglycol, propyleneglycol, cetylstearyl alcohol, carboxymethylcellulose or fatty substances such as hard fat or suitable mixtures thereof, to produce conventional galenic preparations such as plain or coated tablets, capsules, powders, suspensions or suppositories.

The Examples which follow are intended to illustrate the invention:

EXAMPLE I

Methyl 1-acetyl-2-indolinone-5-carboxylate 10.5 g of methyl 2-indolinone-5-carboxylate (prepared analogously to Ogawa et al. Chem. Pharm. Bull 36, 2253–2258 (1988)) are stirred in 30 ml of acetic anhydride for 4 hours at 140° C. Then it is allowed to cool, poured onto ice water and the precipitate is suction filtered. The product is again washed with water, then taken up in methylere chloride, dried over sodium sulphate and concentrated by evaporation.

Yield: 11 g (86% of theory),

Rf value: 0.63 (silica gel; methylene chloride/methanol= 50:1)

EXAMPLE II

Methyl 1-acetyl-3-(1-ethoxy-1-phenyl-methylene)-2-indolinone-5-carboxylate 11 g of methyl 1-acetyl-2-indolinone-5-carboxylate are stirred into 110 ml of acetic anhydride and 30 ml of triethyl orthobenzoate for 2 hours at 100° C. Then the mixture is concentrated by rotary evaporation, the residue is washed with ether and suction filtered.

Yield: 11.5 g (67% of theory),

Rf value: 0.55 (silica gel, methylene chloride/petroleum ether/ethyl acetate=4:5:1)

EXAMPLE III 28.0 g of Rink resin (MBHA resin, Messrs Novobiochem) are allowed to swell in 330 ml of dimethylformamide. Then 330 ml of 30% piperidine in dimethylformamide are added and the mixture is shaken for 7 minutes in order to cleave the FMOC protecting group. The resin is then washed several times with dimethylformamide. Finally, 7.3 g of 2-indolinone-5-carboxylic acid, 5.6 g of hydroxybenzotriazole, 13.3 g of O-(benzotriazol-1-y1)-N,N,N',N'-tetramethyl-uronium-tetrafluoroborate and 5.7 ml of N-ethyl-diisopropylamine in 300 ml of dimethylformamide are added and the mixture is shaken for 1 hour. The solution is then suction filtered and the resin is washed five times with 300 ml of dimethylformamide and three times with 300 ml of methylene chloride. To dry the resin, nitrogen is blown through it.

Yield: 28 g of charged resin

EXAMPLE IV 5 g of the charged resin prepared according to Example III are stirred with 15 ml of acetic anhydride at 8° C. for 1 hour. Then 15 ml of triethyl orthobenzoate are added and the resulting mixture is shaken for a further 3 hours at 110° C. The resin is then suction filtered and washed with dimethylformamide, methanol and finally with methylene chloride.

Yield: 7 g of moist resin

EXAMPLE V 4-(ethylamino-methyl)-nitrobenzene 6 g of 4-nitrobenzylbromide are dissolved in 25 ml of ethanol, mixed with 25 ml of 10% ethanolic ethylamine solution and refluxed for 2 hours. Then the solution is evaporated down, the residue is taken up in methylene chloride and washed with dilute sodium hydroxide solution. Finally, the organic phase is evaporated down.

Yield: 2.3 g (46% of theory),

Rf value: 0.2 (silica gel; methylene chloride/methanol= 9:1)

The following are prepared analogously:

4-[N-(4-chlorophenyl-methyl)-amino-methyl]-nitrobenzene 4-(N-cyclohexyl-amino-methyl)-nitrobenzene 4-(N-isopropyl-amino-methyl)-nitrobenzene 4-(N-butyl-amino-methyl)-nitrobenzene 4-(N-methoxycarbonyl-methyl-amino-methyl)-nitrobenzene 4-(N-(phenyl-methyl)-amino-methyl)-nitrobenzene 4-(pyrrolidino-methyl)-nitrobenzene 4-(morpholino-methyl)-nitrobenzene 4-(pipercidino-methyl)-nitrobenzene 4-(hexamethyleneimino)-nitrobenzene 4-(4-hydroxy-piperidino-methyl)-nitrobenzenee 4-(4-methyl-piperidino-methyl)-nitrobenzene 4-(4-ethyl-piperidino-methyl)-nitrobenzene 4-(4-isopropyl-piperidino-methyl)-nitrobenzene 4-(4-phenyl-piperidino-methyl)-nitrobenzene 4-(4-benzyl-piperidino-methyl)-nitrobenzene 4-(4-ethoxycarbonyl-piperidino-methyl)-nitrobenzene 4-(dimethylamino-methyl)-nitrobenzene 4-(dipropylamino-methyl)-nitrobenzene 4-(4-tert.butyloxycarbonyl-piperazino-methyl)-nitrobenzene 3-(dimethylamino-methyl)-nitrobenzene 4-(2-diethylamino-ethyl)-nitrobenzene 4-(2-morpholinyl-ethyl)-nitrobenzene 4-(2-pyrrolidinyl-ethyl)-nitrobenzene 4-(2-piperidinyl-ethyl)-nitrobenzene
4-(N-ethyl-N-benzyl-amino-methyl)-nitrobenzene
4-(N-propyl-N-benzyl-amino-methyl)-nitrobenzene
4-[N-methyl-N-(4-chlorophenylmethyl)-amino-methyl])-nitrobenzene
4-[N-methyl-N-(4-bromophenylmethyl)-amino-methyl]-nitrobenzene
4-[N-methyl-N-(3-chlorophenylmethyl)-amino-methyl]-nitrobenzene
4-[N-methyl-N-(3,4-dimethoxyphenylmethyl)-amino-methyl]-nitrobenzene
4-[N-methyl-N-(4-methoxyphenylmethyl)-amino-methyl]-nitrobenzene
4-[N-2,2,2-trifluoroethyl-N-(phenylmethyl)-amino-methyl]-nitrobenzene
4-[N-2,2,2-trifluoroethyl-N-(4-chlorophenylmethyl)-amino-methyl]-nitrobenzene

EXAMPLE VI 4-(N-ethyl-N-tert.butoxycarbonyl-amino-methyl)-nitrobenzene 2.2 g of 4-(ethylamino-methyl)-nitrobenzene are dissolved in 50 ml of ethyl acetate and stirred with 2.6 g of di-tert-butyl-dicarbonate for 30 minutes at ambient temperature. Then the solution is washed with water and concentrated by evaporation.

Yield: 3.4 g,

Rf value: 0.9 (silica gel, methylene chloride/methanol= 9:1)

The following are prepared analogously:
4-[N-(4-chlorophenyl-methyl)-N-tert.butoxycarbonyl-amino-methyl]-nitrobenzene
4-(N-cyclohexyl-N-tert.butoxycarbonyl-amino-methyl)-nitrobenzene
4-(N-isopropyl-N-tert.butoxycarbonyl-amino-methyl)-nitrobenzene
4-(N-butyl-N-tert.butoxycarbonyl-amino-methyl)-nitrobenzene
4-(N-methoxycarbonyl-methyl-N-tert.butoxycarbonyl-amino-methyl)-nitrobenzene
4-(N-(phenyl-methyl)-N-tert.butoxycarbonyl-amino-methyl)-nitrobenzene

EXAMPLE VII 4-(N-ethyl-N-tert.butoxycarbonyl-amino-methyl)-aniline 6.4 g cf 4-(N-ethyl-N-tert.butoxycarbonyl-amino-methyl)-nitrobenzene are dissolved in 60 ml of methanol and hydrogenated with 1.5 g of Raney nickel at ambient temperature and hydrogenated under 3 bars of pressure. Then the catalyst is filtered off and the solution is evaporated down.

Yield: 4.78 g,

Rf value: 0.7 (silica gel, methylene chloride/methanol 50:1)

The following are prepared analogously:
4-[N-(4-chlorophenyl-methyl)-N-tert.butoxycarbonyl-amino-methyl]-aniline
4-(N-cyclohexyl-N-tert.butoxycarbonyl-amino-methyl)-aniline
4-(N-isopropyl-N-tert.butoxycarbonyl-amino-methyl)-aniline
4-(N-butyl-N-tert.butoxycarbonyl-amino-methyl)-aniline
4-(N-methoxycarbonyl-methyl-N-tert.butoxycarbonyl-amino-methyl)-aniline
4-(N-(phenyl-methyl)-N-tert.butoxycarbonyl-amino-methyl)-aniline
4-(pyrrolidino-methyl)-aniline
4-(morpholino-methyl)-aniline
4-(piperidino-methyl)-aniline
4-(hexamethyleneimino-methyl)-aniline
4-(4-hydroxy-piperidino-methyl)-aniline
4-(4-methyl-piperidino-methyl)-aniline
4-(4-ethyl-piperidino-methyl)-aniline
4-(4-isopropyl-piperidino-methyl)-aniline
4-(4-phenyl-piperidino-methyl)-aniline
4-(4-benzyl-piperidino-methyl)-aniline
4-(4-ethoxycarbonyl-piperidino-methyl)-aniline
4-(dimethylamino-methyl)-aniline
4-(dipropylamino-methyl)-aniline
4-(4-tert.butoxycarbonyl-piperazinyl-methyl)--aniline
3-(dimethylamino-methyl)-aniline
4-(2-diethylamino-ethyl)-aniline
4-(2-morpholinyl-ethyl)-aniline
4-(2-pyrrolidinyl-ethyl)-aniline
4-(2-piperidinyl-ethyl)-aniline
4-(N-ethyl-N-benzyl-amino-methyl)-aniline
4-(N-propyl-N-benzyl-amino-methyl)-aniline
4-[N-methyl-N-(4-chlorophenylmethyl)-amino-methyl]-aniline
4-[N-methyl-N-(4-bromophenylmethyl)-amino-methyl]-aniline
4-[N-methyl-N-(3-chlorophenylmethyl)-amino-methyl]-aniline
4-[N-methyl-N-(3,4-dimethoxyphenylmethyl)-amino-methyl]-aniline
4-[N-methyl-N-(4-methoxyphenylmethyl)-amino-methyl]-aniline 4-[N-2,2,2-trifluoroethyl-N-(phenylmethyl)-amino-methyl]-aniline 4-[N-2,2,2-trifluoroethyl-N-(4-chlorophenylmethyl)-amino-methyl]-aniline Preparation of the end products:

EXAMPLE 1

Methyl 3-Z-[1-(1-methyl-piperidin-4-y1-amino)-1-phenyl-methylene]-2-indolinone-5-carboxylate 11.5 g of methyl 1-acetyl-3-(1-ethoxy-1-phenyl-methylene)-2-indolinine-5-carboxylate are dissolved in 115 ml of methylene chloride and stirred with 10.8 g of 4-amino-N-methylpiperidine for 5 hours at ambient temperature. Then 20 ml of methanolic ammonia are added and the mixture is left to stand overnight. The solution is evaporated down and the residue is washed with ether.

Yield: 11.9 g (97% of theory),

Rf value: 0.20 (silica gel; methylene chloride/methanol= 9:1)

$C_{23}H_{25}N_3O_3$

Mass spectrum: m/z=391 (M$^+$)

The following are prepared analogously:
(1) methyl 3-Z-[1-(4-(piperidino-methyl)-phenylamino)-1-phenyl-methylene]-2-indolinone-5-carboxylate Rf value: 0.4 (silica gel, methylene chloride/methanol= 9:1)

$C_{29}H_{29}N_3O_3$
mass spectrum: m/z=467 (M⁺)

(2) methyl 3-Z-[1-(4-(N-phenylmethyl-N-methylamino-methyl)-phenylamino)-1-phenyl-methylene]-2-indolinone-5-carboxylate
$C_{32}H_{29}N_3O_3$
mass spectrum: m/z=503 (M⁺)

(3) methyl 3-Z-[1-(4-(dimethylamino-methyl)-phenylamino)-1-phenyl-methylene]-2-indolinone-5-carboxylate
$C_{26}H_{25}N_3O_3$
mass spectrum: m/z=427 (M⁺)

(4) methyl 3-Z-[1-(3-(dimethylamino-methyl)-phenylamino)-1-phenyl-methylene]-2-indolinone-5-carboxylate
$C_{26}H_{26}N_3O_3$
mass spectrum: m/z=427 (M⁺)

(5) methyl 3-Z-[1-(4-chlorophenylamino)-1-phenyl-methylene]-2-indolinone-5-carboxylate (6) methyl 3-Z-(1-phenylamino-1-phenyl-methylene)-2-indolinone-5-carboxylate

EXAMPLE 2

3-Z-[1-(1-methyl-piperidine-4-y1-amino)-1-phenyl-methylene]-2-indolinone-5-carboxylic acid 11.9 g of methyl 3-Z-[1-(1-methyl-piperidin-4-y1-amino)-1-phenyl-methylene]-2-indolinone-5-carboxylate are refluxed in 300 ml of methanol and 150 ml of 1N sodium hydroxide solution for 4 hours. Then the mixture is neutralised with 150 ml of 1N hydrochloric acid and evaporated to dryness. The residue is washed with water several times and dried.

Yield: 86% of theory,

Rf value: 0.17 (silica gel; methylene chloride/methanol= 4:1)

$C_{22}H_{23}N_3O_3$

Mass spectrum: m/z=377 (M⁺)

The following are prepared analogously:

(1) 3-Z-[1-(4-(piperidino-methyl)-phenylamino)-1-phenyl-methylene]-2-indolinone-5-carboxylic acid Rf value: 0.15 (silica gel, methylene chloride/methanol= 9:1)
$C_{28}H_{27}N_3O_3$
mass spectrum: m/z=453 (M⁺)

(2) 3-Z-[1-(4-(N-phenylmethyl-N-methylamino-methyl)-phenyl-amino)-phenyl-methylene)-2-indolinone-5-carboxylic acid
$C_{31}H_{27}N_3O_3$
mass spectrum: m/z=489 (M⁺)

(3) 3-Z-[1-(4-(dimethylamino-methyl)-phenylamino)-1-phenyl-methylene]-2-indolinone-5-carboxylic acid
$C_{25}H_{23}N_3O_3$
mass spectrum: m/z=413 (M⁺)

(4) 3-Z-[1-(3-(dimethylamino-methyl)-phenylamino)-1-phenyl-methylene) -2-indolinone-5-carboxylic acid
$C_{25}H_{23}N_3O_3$
mass spectrum: m/z=413 (M⁺)

(5) 3-Z-[1-(4-chlorophenylamino)-1-phenyl-methylene]-2-indolinone-5-carboxylic acid (6) 3-Z-[1-phenylamino-1-phenyl-methylene)-2-indolinone-5-carboxylic acid

EXAMPLE 3

3-Z-[1-(1-methyl-piperidine-4-y1-amino)-1-phenyl-methylene]-5-dimethylcarbamoyl-2-indolinone 2 g of 3-Z-[1-(1-methyl-piperidin-4-y1-amino)-1-phenyl-methylene]-2-indolinone-5-carboxylic acid are refluxed with 5 ml of thionyl chloride for 2 hours. Then the mixture is concentrated by rotary evaporation and the residue is washed with ether. 0.5 g of this acid chloride are taken up in 5 ml of methylene chloride without further purification and mixed with 0.5 ml of dimethylamine in 5 ml of methylene chloride and stirred overnight at ambient temperature. The product is chromatographed over a silica gel column with methylene chloride/methanol/ammonia (4:1:0.1).

Yield: 50% of theory,

Rf value: 0.14 (silica gel: methylene chloride/methanol= 9:1)

$C_{24}H_{28}N_4O_2$

Mass spectrum: m/z=404 (M⁺)

The following compounds are prepared analogously:

(1) 3-Z-[1-(1-methyl-piperidin-4-y1-amino)-1-phenyl-methylene]-5-methylcarbamoyl-2-indolinone
Yield: 49% of theory,
Rf value: 0.19 (silica gel; methylene chloride/methanol= 4:1)
$C_{23}H_{26}N_4O_2$
Mass spectrum: m/z=390 (M⁺)

(2) 3-Z-[1-(1-methyl-piperidin-4-y1-amino)-1-phenyl-methylene]-5-carbamoyl-2-indolinone
Yield: 58% of theory,
Rf value: 0.15 (silica gel; methylene chloride/methanol 4:1)
$C_{22}H_{24}N_4O_2$
Mass spectrum: m/z=376 (M⁺)

(3) 3-Z-[1-(4-piperidino-methyl-phenylamino)-1-phenyl-methylene]-5-dimethylcarbamoyl-2-indolinone Prepared from 3-Z-[1-(4-piperidino-methyl-phenylamino)-1-phenyl-methylene]-2-indolinone-5-carboxylic acid and dimethylamine or 0.64 g of Z-[1-(4-piperidino-methyl-phenylamino)-1-phenyl-methylene]-2-indolinone-5-carboxylic acid, 0.34 g of dimethylamine hydrochloride, 0.9 g of O-benzotriazol-1-y1-N,N,N',N'-tetramethyluronium-tetrafluoroborate), 0.4 g of 1-hydroxy-1H-benzotriazole and 2.9 g of diisopropylethylamine are stirred in 20 ml of dimethylformamide for 20 hours at ambient temperature. The mixture is then evaporated down and the residue is suspended in water. The precipitate is suction filtered.

Yield: 600 mg (88% of theory),
Rf value: 0.2 (silica gel, methylene chloride/ethanol=9:1)
$C_{30}H_{32}N_4O_2$
mass spectrum: m/z=481 (M+H)⁺

(4) 3-Z-[1-(4-piperidino-methyl-phenylamino)-1-phenyl-methylene]-5-methylcarbamoyl-2-indolinone Prepared from 3-Z-[1-(4-piperidino-methyl-phenylamino)-1-phenyl-methylene]-2-indolinone-5-carboxylic acid and methylamine analogously to Example 3(3).
Rf value: 0.2 (silica gel, methylene chloride/ethanol=9:1)
$C_{29}H_{30}N_4O_2$
mass spectrum: m/z=467 (M+H)⁺

(5) 3-Z-(1-(4-piperidino-methyl-phenylamino)-1-phenyl-methylene]-5-methylethylcarbamoyl-2-indolinone Prepared from 3-Z-[1-(4-piperidino-methyl-phenylamino)-1-phenyl-methylene]-2-indolinone-5-carboxylic acid and methyl-ethylamine analogously to Example 3(3).
Rf value: 0.55 (silica gel, methylene chloride/ethanol= 9:1)

C₃₁H₃₄N₄O₂
mass spectrum: m/z=495 (M+H)⁺

(6) 3-Z-[1-(4-piperidino-methyl-phenylamino)-1-phenyl-methylene]-5-propylcarbamoyl-2-indolinone Prepared from 3-Z-[1-(4-piperidino-methyl-phenylamino)-1-phenyl-methylene]-2-indolinone-5-carboxylic acid and propylamine analogously to Example 3(3).

Rf value: 0.31 (silica gel, methylene chloride/ethanol= 9:1)

C₃₁H₃₄N₄O₂
mass spectrum: m/z=495 (M+H)⁺

(7) 3-Z-[1-(4-piperidino-methyl-phenylamino)-1-phenyl-methylene]-5-diethylcarbamoyl-2-indolinone Prepared from 3-Z-[1-(4-piperidino-methyl-phenylamino)-1-phenyl-methylene]-2-indolinone-5-carboxylic acid and diethylamine analogously to Example 3(3).

Rf value: 0.55 (silica gel, methylene chloride/ethanol= 9:1)

C₃₂H₃₆N₄O₂
mass spectrum: m/z=509 (M+H)⁺

(8) 3-Z-[1-(4-(N-phenylmethyl-N-methyl-aminomethyl)-phenylamino)-1-phenyl-methylene]-5-methylcarbamoyl-2-indolinone (9) 3-Z-[1-(4-(N-phenylmethyl-N-methyl-aminomethyl)-phenyl-amino)-1-phenyl-methylene]-5-dimethylcarbamoyl-2-indolinone 3-Z-[1-(4-(N-phenylmethyl-N-methyl-aminomethyl)-phenyl-amino)-1-phenyl-methylene]-5-diethylcarbamoyl-2-indolinone 3-Z-[1-(4-(N-phenylmethyl-N-methyl-aminomethyl)-phenyl-amino)-1-phenyl-methylene]-5-propylcarbamoyl-2-indolinone

(12) 3-Z-[1-(4-(N-phenylmethyl-N-methyl-aminomethyl)-phenyl-mino)-1-phenyl-methylene]-5-dipropylcarbamoyl-2-indolinone

(13) 3-Z-[1-(4-(dimethylamino-methyl)-phenylamino)-1-phenyl-ethylene]-5-methylcarbamoyl-2-indolinone

(14) 3-Z-[1-(4-(dimethylamino-methyl)-phenylamino)-1-phenyl-methylene]-5-dimethylcarbamoyl-2-indolinone

(15) 3-Z-[1-(4-(dimethylamino-methyl)-phenylamino-1-phenyl-methylene]-5-diethylcarbamoyl-2-indolinone

(16) 3-Z-[1-(4-(dimethylamino-methyl)-phenylamino)-1-phenyl-methylene]-5-propylcarbamoyl-2-indolinone

(17) 3-Z-[1-(4-(dimethylamino-methyl)-phenylamino)-1-phenyl-methylene]-5-dipropylcarbamoyl-2-indolinone

(18) 3-Z-[1-(3-(dimethylamino-methyl)-phenylamino)-1-phenyl-methylene]-5-methylcarbamoyl-2-indolinone

(19) 3-Z-[1-(3-(dimethylamino-methyl)-phenylamino)-1-phenyl-methylene]-5-dimethylcarbamoyl-2-indolinone

(20) 3-Z-[1-(3-(dimethylamino-methyl)-phenylamino)-1-phenyl-methylene]-5-diethylcarbamoyl-2-indolinone

(21) 3-Z-[1-(3-(dimethylamino-methyl)-phenylamino)-1-phenyl-methylene]-5-propylcarbamoyl-2-indolinone

(22) 3-Z-[1-(3-(dimethylamino-methyl)-phenylamino)-1-phenyl-methylene]-5-dipropylcarbamoyl-2-indolinone

(23) 3-Z-[1-(4-chlorophenylamino)-1-phenyl-methylene]-5-methylcarbamoyl-2-indolinone

(24) 3-Z-[1-(4-chlorophenylamino)-1-phenyl-methylene]-5-dimethylcarbamoyl-2-indolinone

(25) 3-Z-[1-(4-chlorophenylamino-1-phenyl-methylene]-5-diethylcarbamoyl-2-indolinone

(26) 3-Z-[1-(4-chlorophenylamino)-1-phenyl-methylene]-5-propylcarbamoyl-2-indolinone

(27) 3-Z-[1-(4-chlorophenylamino)-1-phenyl-methylene]-5-dipropylcarbamoyl-2-indolinone

(28) 3-7-(1-phenylamino-1-phenyl-methylene)-5-methylcarbamoyl-2-indolinone

(29) 3-7-(1-phenylamino-1-phenyl-methylene)-5-dimethylcarbamoyl-2-indolinone

(30) 3-Z-(1-phenylamino-1-phenyl-methylene)-5-diethylcarbamoyl-2-indolinone

(31) 3-Z-(1-phenylamino-1-phenyl-methylene)-5-propylcarbamoyl-2-indolinone

(32) 3-Z-(1-phenylamino-1-phenyl-methylene)-5-dipropylcarbamoyl-2-indolinone

EXAMPLE 4

3-Z-[1-(4-amino-phenylamino)-1-phenyl-methylene]-5-amido-2-indolinone 800 mg of resin prepared according to Example IV are suspended in 4 ml of methylene chloride and shaken with 0.8 g of 1,4-phenylenediamine for 16 hours at ambient temperature. The mixture is filtered and the resin is washed several times with methylene chloride, methanol and dimethylformamide. Then 3 ml of methanolic ammonia is added for 2 hours in order to eliminate the acetyl group. Finally, after further washing, 4 ml of 10% trifluoroacetic acid in methylene chloride is added over a period of 90 minutes, the resin is separated off and the solution is evaporated down. The residue is taken up in a little 1N sodium hydroxide solution and extracted with methylene chloride. The organic phase is dried over sodium sulphate and concentrated by rotary evaporation.

Yield: 45 mg (30% of theory over all the steps),

Rf value: 0.26 (silica gel; methylene chloride/methanol= 9:1)

C₂₂H₁₈N₄O₂
Mass spectrum: m/z=370 (M⁺)

The following compounds are prepared analogously:

(1) 3-Z-[1-(3-amino-phenylamino)-1-phenyl-methylene]-5-amido-2-indolinone

Yield: 24% of theory,

Rf value: 0.44 (silica gel; methylene chloride/methanol= 9:1)

C₂₂H₁₈N₄O₂
Mass spectrum: m/z=370 (M⁺)

(2) 3-Z-(1-phenylamino)-1-phenyl-methylene)-5-amido-2-indolinone

Yield: 27% of theory,

Rf value: 0.53 (silica gel; methylene chloride/methanol= 9:1)

C₂₂H₁₇N₃O₂
Mass spectrum: m/z=355 (M⁺)

(3) 3Z-[1-(4-acetylamino-phenylamino)-1-phenyl-methylene]-5-amido-2-indolinone

Yield: 28% of theory,

Rf value: 0.35 (silica gel; methylene chloride/methanol= 9:1)

C₂₄H₂₀N₄O₃
Mass spectrum: m/z=412 (M⁺)

(4) 3-Z-[1-(4-acetyl-N-methyl-amino-phenylamino)-1-phenyl-methylene]-5-amido-2-indolinone Yield: 15% of theory, Rf value: 0.36 (silica gel; methylene chloride/methanol= 9:1)

C₂₅H₂₂N₄O₃
Mass spectrum: m/z=426 (M⁺)

(5) 3-Z-[1-(4-(2-amino-ethyl)-phenylamino)-1-phenyl-methylene]-5-amido-2-indolinone
Yield: 30% of theory,
Rf value: 0.04 (silica gel; methylene chloride/methanol= 9:1)
$C_{24}H_{22}N_4O_2$
Mass spectrum: m/z=398 (M⁺)

(6) 3-Z-[1-(4-methoxy-phenylamino)-1-phenyl-methylene]-5-amido-2-indolinone
Yield: 32% of theory,
Rf value: 0.48 (silica gel; methylene chloride/methanol= 9:1)
$C_{23}H_{19}N_3O_3$
Mass spectrum: m/z=385 (M⁺)

(7) 3-Z-[1-(4-biphenylamino)-1-phenyl-methylene]-5-amido-2-indolinone
Yield: 22% of theory,
Rf value: 0.51 (silica gel; methylene chloride/methanol= 9:1)
$C_{28}H_{21}N_3O_2$
Mass spectrum: m/z=431 (M⁺)

(8) 3-Z-[1-(3-pyridylamino)-1-phenyl-methylene]-5-amido-2-indolinone
Yield: 35% of theory,
Rf value: 0.41 (silica gel; methylene chloride/methanol= 9:1)
$C_{21}H_{16}N_4O_2$
Mass spectrum: m/z=356 (M⁺)

(9) 3-Z-[1-(4-dimethylamino-phenylamino)-1-phenyl-methylene]-5-amido-2-indolinone
Yield: 19% of theory,
Rf value: 0.49 (silica gel; methylene chloride/methanol= 9:1)
$C_{24}H_{22}N_4O_2$
Mass spectrum: m/z=398 (M⁺)

(10) 3-Z-[1-(4-morpholino-phenylamino)-1-phenyl-methylene]-5-amido-2-indolinone
Yield: 42% of theory,
Rf value: 0.48 (silica gel; methylene chloride/methanol= 9:1)
$C_{26}H_{24}N_4O_3$
Mass spectrum: m/z=440 (M⁺)

(11) 3-Z-[1-(4-tert.butyl-phenylamino)-1-phenyl-methylene]-5-amido-2-indolinone
Yield: 32% of theory,
Rf value: 0.48 (silica gel; methylene chloride/methanol= 9:1)
$C_{26}H_{25}N_3O_3$
Mass spectrum: m/z=411 (M⁺)

(12) 3-Z-[1-(2-amino-phenylamino)-1-phenyl-methylene]-5-amido-2-indolinone
Yield: 28% of theory,
Rf value: 0.52 (silica gel; methylene chloride/methanol= 9:1)
$C_{22}H_{18}N_4O_2$
Mass spectrum: m/z=370 (M⁺)

(13) 3-Z-[1-(4-benzyloxy-phenylamino)-1-phenyl-methylene]-5-amido-2-indolinone
Yield: 40% of theory,
Rf value: 0.4 (silica gel; methylene chloride/methanol= 9:1)
$C_{29}H_{23}N_3O_3$
Mass spectrum: m/z=461 (M⁺)

(14) 3-Z-[1-(4-bromophenylamino)-1-phenyl-methylene]-5-amido-2-indolinone
Yield: 35% of theory,
Rf value: 0.46 (silica gel; methylene chloride/methanol= 9:1)
$C_{22}H_{16}BrN_3O_2$
Mass spectrum: m/z=433/435 (M⁺)

(15) 3-Z-[1-(4-methoxycarbonyl-phenylamino)-1-phenyl-methylene]-5-amido-2-indolinone
Yield: 34% of theory,
Rf value: 0.36 (silica gel; methylene chloride/methanol= 9:1)
$C_{24}H_{19}N_3O_4$
Mass spectrum: m/z=413 (M⁺)

(16) 3-Z-[1-(3-amido-phenylamino)-1-phenyl-methylene]-5-amido-2-indolinone
Yield: 32% of theory,
Rf value: 0.32 (silica gel; methylene chloride/methanol= 9:1)
$C_{23}H_{18}N_4O_3$
Mass spectrum: m/z=398 (M⁺)

(17) 3-Z-[1-(3-methyl-phenylamino)-1-phenyl-methylene]-5-amido-2-indolinone
Yield: 12% of theory,
Rf value: 0.5 (silica gel; methylene chloride/methanol= 9:1)
$C_{23}H_{19}N_3O_2$
Mass spectrum: m/z=369 (M⁺)

(18) 3-Z-[1-(2-methyl-phenylamino)-1-phenyl-methylene]-5-amido-2-indolinone
Yield: 21% of theory,
Rf value: 0.5 (silica gel; methylene chloride/methanol= 9:1)
$C_{23}H_{19}N_3O_2$
Mass spectrum: m/z=369 (M⁺)

(19) 3-Z-1-(3-methoxy-phenylamino)-1-phenyl-methylene]-5-amido-2-indolinone
Rf value: 0.49 (silica gel; methylene chloride/methanol= 9:1)
$C_{23}H_{19}N_3O_3$
Mass spectrum: m/z=385 (M⁺)

(20) 3-Z-[1-(3-ethoxycarbonyl-phenylamino)-1-phenyl-methylene]-5-amido-2-indolinone
Rf value: 0.48 (silica gel; methylene chloride/methanol= 9:1)
$C_{25}H_{21}N_3O_4$
Mass spectrum: m/z=427 (M⁺)

(21) 3-Z-[1-(3-nitro-phenylamino)-1-phenyl-methylene]-5-amido-2-indolinone
Yield: 32% of theory,
Rf value: 0.56 (silica gel; methylene chloride/methanol= 9:1)
$C_{22}H_{16}N_4O_4$
Mass spectrum: m/z=400 (M⁺)

(22) 3-Z-[1-(4-amido-phenylamino)-1-phenyl-methylene]-5-amido-2-indolinone
Yield: 26% of theory,
Rf value: 0.47 (silica gel; methylene chloride/methanol= 9:1)
$C_{23}H_{18}N_4O_3$
Mass spectrum: m/z=398 (M⁺)

(23) 3-Z-[1-(4-pyridylamino)-1-phenyl-methylene]-5-amido-2-indolinone
Yield: 15% of theory,
Rf value: 0.42 (silica gel; methylene chloride/methanol= 9:1)
$C_{21}H_{16}N_4O_2$
Mass spectrum: m/z=356 (M⁺)

(24) 3-Z-[1-(4-methyl-phenylamino)-1-phenyl-methylene]-5-amido-2-indolinone

Yield: 45% of theory,
Rf value: 0.54 (silica gel; methylene chloride/methanol=9:1)
$C_{23}H_{19}N_3O_2$
Mass spectrum: m/z=369 (M⁺)

(25) 3-Z-[1-(4-ethoxy-phenylamino)-1-phenyl-methylene]-5-amido-2-indolinone
Yield: 40% of theory,
Rf value: 0.51 (silica gel; methylene chloride/methanol=9:1)
$C_{24}H_{21}N_3O_3$
Mass spectrum: m/z=399 (M⁺)

(26) 3-Z-[1-(3-bromophenylamino)-1-phenyl-methylene]-5-amido-2-indolinone
Yield: 41% of theory,
Rf value: 0.53 (silica gel; methylene chloride/methanol=9:1)
$C_{22}H_{16}BrN_3O_2$
Mass spectrum: m/z=433/435 (M⁺)

(27) 3-Z-[1-(4-chlorophenylamino)-1-phenyl-methylene]-5-amido-2-indolinone
Yield: 50% of theory,
Rf value: 0.49 (silica gel; methylene chloride/methanol=9:1)
$C_{22}H_{16}ClN_3O_2$
Mass spectrum: m/z=389 (M⁺)

(28) 3-Z-[1-(4-isopropyl-phenylamino)-1-phenyl-methylene]-5-amido-2-indolinone
Yield: 48% of theory,
Rf value: 0.65 (silica gel; methylene chloride/methanol=9:1)
$C_{25}H_{23}N_3O_2$
Mass spectrum: m/z=397 (M⁺)

(29) 3-Z-[1-(2-fluorenylamino)-1-phenyl-methylene]-5-amido-2-indolinone
Yield: 43% of theory,
Rf value: 0.58 (silica gel; methylene chloride/methanol=9:1)
$C_{29}H_{21}N_3O_3$
Mass spectrum: m/z=443 (M⁺)

(30) 3-Z-[1-(4-(2-hydroxyethyl)-phenylamino)-1-phenyl-methylene]-5-amido-2-indolinone
Yield: 22% of theory,
Rf value: 0.37 (silica gel; methylene chloride/methanol=9:1)
$C_{24}H_{21}N_3O_3$
Mass spectrum: m/z=398 (M–H)

(31) 3-Z-[1-(4-(4-imidazolyl)-phenylamino)-1-phenyl-methylene]-5-amido-2-indolinone
Yield: 23% of theory,
Rf value: 0.5 (silica gel; methylene chloride/methanol=9:1)
$C_{25}H_{19}N_5O_2$
Mass spectrum: m/z=421 (M⁺)

(32) 3-Z-[1-(4-ethoxycarbonylmethyl-phenylamino)-1-phenyl-methylene]-5-amido-2-indolinone
$C_{26}H_{23}N_3O_4$
Mass spectrum: m/z=442 (M+H)⁺

(33) 3-Z-[1-(4-bromo-3-methyl-phenylamino)-1-phenyl-methylene]-5-amido-2-indolinone
$C_{23}H_{18}BrN_3O_2$
Mass spectrum: m/z=447/449 (M⁺)

(34) 3-Z-[1-(4-cyclohexyl-phenylamino)-1-phenyl-methylene]-5-amido-2-indolinone
$C_{28}H_{27}N_3O_2$
Mass spectrum: m/z=437 (M⁺)

(35) 3-Z-[1-(4-bromo-2-methyl-phenylamino)-1-phenyl-methylene]-5-amido-2-indolinone
$C_{23}H_{18}BrN_3O_2$
Mass spectrum: m/z=447/449 (M⁺)

(36) 3-Z-(1-amino-1-phenyl-methylene)-5-amido-2-indolinone
Rf value: 0.3 (silica gel; methylene chloride/methanol=9:1)
$C_{16}H_{13}N_3O_2$
Mass spectrum: m/z=279 (M⁺)

(37) 3-Z-(1-cyclohexylamino-1-phenyl-methylene)-5-amido-2-indolinone
Rf value: 0.55 (silica gel; methylene chloride/methanol=9:1)
$C_{22}H_{23}N_3O_2$
Mass spectrum: m/z=361 (M⁺)

(38) 3-Z-(1-cyclopentylamino-1-phenyl-methylene)-5-amido-2-indolinone
Rf value: 0.53 (silica gel; methylene chloride/methanol=9:1)
$C_{21}H_{21}N_3O_2$
Mass spectrum: m/z=347 (M⁺)

(39) 3-Z-(1-methylamino-1-phenyl-methylene)-5-amido-2-indolinone
Rf value: 0.5 (silica gel; methylene chloride/methanol=9:1)
$C_{17}H_{15}N_3O_2$
Mass spectrum: m/z=293 (M⁺)

(40) 3-Z-(1-ethylamino-1-phenyl-methylene)-5-amido-2-indolinone
Rf value: 0.52 (silica gel; methylene chloride/methanol=9:1)
$C_{18}H_{17}N_3O_2$
Mass spectrum: m/z=307 (M⁺)

(41) 3-Z-(1-isopropylamino-1-phenyl-methylene)-5-amido-2-indolinone
Rf value: 0.44 (silica gel; methylene chloride/methanol=9:1)
$Cl_{19}H_{19}N_3O_2$
Mass spectrum: m/z=321 (M⁺)

(42) 3-Z-(1-dimethylamino-1-phenyl-methylene)-5-amido-2-indolinone
Rf value: 0.39 (silica gel; methylene chloride/methanol=9:1)
$C_{18}H_{17}N_3O_2$
Mass spectrum: m/z=307 (M⁺)

(43) 3-Z-(1-cyclopropylamino-1-phenyl-methylene)-5-amido-2-indolinone
Rf vaLue: 0.47 (silica gel; methylene chloride/methanol=9:1)
$C_{19}H_{17}N_3O_2$
Mass spectrum: m/z=319 (M⁺)

(44) 3-Z-(1-cycloheptylamino-1-phenyl-methylene)-5-amido-2-indolinone
Rf value: 0.58 (silica gel; methylene chloride/methanol=9:1)
$C_{23}H_{25}N_3O_2$
Mass spectrum: m/z=375 (M⁺)

(45) 3-Z-(1-cyclobutylamino-1-phenyl-methylene)-5-amido-2-indolinone
Rf value: 0.49 (silica gel; methylene chloride/methanol=9:1)
$C_{20}H_{19}N_3O_2$
Mass spectrum: m/z=333 (M⁺)

(46) -Z-[1-(4-methylcyclohexylamino)-1-phenyl-methylene]-5-amido-2-indolinone
Rf value: 0.67 (silica gel; methylene chlcride/methanol= 9:1)
$C_{23}H_{25}N_3O_2$
Mass spectrum: m/z=375 (M⁺)

(47) 3-Z-[1-(1-(R,S)-indanylamino)-1-phenyl-methylene]-5-amido-2-indolinone
Rf value: 0.59 (silica gel; methylene chloride/methanol= 9:1)
$C_{25}H_{21}N_3O_2$
Mass spectrum: m/z=395 (M⁺)

(48) 3-Z-[1-(methoxycarbonylmethylamino)-1-phenyl-methylene]-5-amido-2-indolinone
Rf vaLue: 0.46 (silica gel; methylene chloride/methanol= 9:1)
$C_{19}H_{17}N_3O_4$
Mass spectrum: m/z=351 (M⁺)

(49) 3-Z-[1-((2-methoxycarbonyl-ethyl)-amino)-1-phenyl-methylene]-5-amido-2-indolinone
Rf value: 0.45 (silica gel; methylene chloride/methanol= 9:1)
$C_{20}H_{19}N_3O_4$
Mass spectrum: m/z=365 (M⁺)

(50) 3-Z-[1-(4-aminomethyl-phenylamino)-1-phenyl-methylene]-5-amido-2-indolinone
Yield: 32% of theory,
Rf value: 0.46 (silica gel; methylene chloride/methanol= 9:1)
$C_{23}H_{20}N_4O_2$
Mass spectrum: m/z=384 (M⁺)

(51) 3-Z-[1-(4-pyrrolidinomethyl-phenylamino)-1-phenyl-methylene]-5-amido-2-indolinone-trifluoroacetate
Yield: 60% of theory,
Rf value: 0.07 (silica gel; methylene chloride/methanol= 9:1)
$C_{27}H_{26}N_4O_2$
Mass spectrum: m/z=438 (M⁺)

(52) 3-Z-[1-(4-morpholinomethyl-phenylamino)-1-phenyl-methylene]-5-amido-2-indolinone
Yield: 65% of theory,
Rf value: 0.46 (silica gel; methylene chloride/methanol= 9:1)
$C_{27}H_{26}N_4O_3$
Mass spectrum: m/z=454 (M⁺)

(53) 3-Z-[1-(4-piperidinomethyl-phenylamino)-1-phenyl-methylene]-5-amido-2-indolinone-trifluoroacetate
Yield: 60% of theory,
Rf value: 0.08 (silica gel; methylene chloride/methanol= 9:1)
$C_{28}H_{28}N_4O_2$
Mass spectrum: m/z=452 (M⁺)

(54) 3-Z-[1-(4-hexamethyleneiminomethyl-phenylamino)-1-phenyl-methylene]-5-amido-2-indolinone-trifluoroacetate
$C_{29}H_{30}N_4O_2$
Mass spectrum: m/z=466 (M⁺)

(55) 3-Z-[1-(4-(4-hydroxy-piperidinomethyl)-phenylamino)-1-phenyl-methylene]-5-amido-2-indolinone
$C_{28}H_{28}N_4O_3$
Mass spectrum: m/z=468 (M⁺)

(56) 3-Z-[1-(4-(4-methyl-piperidinomethyl)-phenylamino)-1-phenyl-methylene]-5-amido-2-indolinone
$C_{29}H_{30}N_4O_2$
Mass spectrum: m/z=466 (M⁺)

(57) 3-Z-[1-(4-(4-ethyl-piperidinomethyl)-phenylamino)-1-phenyl-methylene]-5-amido-2-indolinone
$C_{30}H_{32}N_4O_2$
Mass spectrum: m/z=480 (M⁺)

(58) 3-Z-[1-(4-(4-isopropyl-piperidinomethyl)-phenylamino)-1-phenyl-methylene]-5-amido-2-indolinone
$C_{31}H_{34}N_4O_2$
Mass spectrum: m/z=494 (M⁺)

(59) 3-Z-[1-(4-(4-phenyl-piperidinomethyl)-phenylamino)-1-phenyl-methylene]-5-amido-2-indolinone
$C_{34}H_{32}N_4O_2$
Mass spectrum: m/z=528 (M⁺)

(60) 3-Z-[1-(4-(4-benzyl-piperidinomethyl)-phenylamino)-1-phenyl-methylene]-5-amido-2-indolinone
$C_{35}H_{34}N_4O_2$
Mass spectrum: m/z=0 542 (M⁺)

(61) 3-Z-[1-(4-(4-ethoxycarbonyl-piperidinomethyl)-phenyl-amino)-1-phenyl-methylene]-5-amido-2-indolinone
$C_{31}H_{32}N_4O_4$
Mass spectrum: m/z=524 (M⁺)

(62) 3-Z-[1-(4-dimethylaminomethyl-phenylamino)-1-phenyl-methylene]-5-amido-2-indolinone
Mass spectrum: m/z=412 (M⁺)

(63) 3-Z-[1-(4-dipropylaminomethyl-phenylamino)-1-phenyl-methylene]-5-amido-2-indolinone
$C_{29}H_{32}N_4O_2$
Mass spectrum: m/z=468 (M⁺)

(64) 3-Z-[1-(4-piperazinylmethyl-phenylamino)-1-phenyl-methylene]-5-amido-2-indolinone
$C_{27}H_{27}N_5O_2$
Mass spectrum: m/z=453 (M⁺)

(65) 3-Z-[1-(3-dimethylaminomethyl-phenylamino)-1-phenyl-methylene]-5-amido-2-indolinone
Mass spectrum: m/z=412 (M⁺)

(66) 3-Z-[1-(4-(2-diethylamino-ethyl)-phenylamino)-1-phenyl-methylene]-5-amido-2-indolinone
C28H30N4O₂
Mass spectrum: m/z=454 (M⁺)

(67) 3-Z-[1-(4-(2-morpholino-ethyl)-phenylamino)-1-phenyl-methylene]-5-amido-2-indolinone
$C_{28}H_{28}N_4O_3$
Mass spectrum: m/z=468 (M⁺)

(68) 3-Z-[1-(4-(2-pyrrolidinyl-ethyl)-phenylamino)-1-phenyl-methylene]-5-amido-2-indolinone
$C_{28}H_{28}N_4O_2$
Mass spectrum: m/z=452 (M⁺)

(69) 3-Z-[1-(4-(2-piperidinyl-ethyl)-phenylamino)-1-phenyl-methylene]-5-amido-2-indolinone
$C_{29}H_{30}N_4O_2$
Mass spectrum: m/z=466 (M⁺)

(70) 3-Z-1-(2-thiazolylamino)-1-phenyl-methylene]-5-amido-2-indolinone
Yield: 30% of theory,
Rf value: 0.48 (silica gel; methylene chloride/methanol= 9:1)
$C_{19}H_{14}N_4O_2S$
Mass spectrum: m/z=362 (M⁺)

(71) 3-Z-[1-(2-benzimidazolylamino)-1-phenyl-methylene]-5-amido-2-indolinone

Yield: 29% of theory,
Rf value: 0.44 (silica gel; methylene chloride/methanol=9:1)
$C_{23}H_{17}N_5O_2$
Mass spectrum: m/z=395 (M⁺)

(72) 3-Z-[1-(5-methyl-isoxazol-3-yl-amino)-1-phenyl-methylene]-5-amido-2-indolinone Yield: 39% of theory,
Rf value: 0.43 (silica gel; methylene chloride/methanol=9:1)
$C_{21}H_{18}N_4O_3$
Mass spectrum: m/z=374 (M⁺)

(73) 3-Z-(1-benzylamino-1-phenyl-methylene)-5-amido-2-indolinone

Rf value: 0.63 (silica gel; methylene chloride/methanol=9:1)
$C_{23}H_{19}N_3O_2$
Mass spectrum: m/z=369 (M⁺)

(74) 3-Z-[1-(4-(1-imidazolyl-methyl)-phenyLamino)-1-phenyl-methylene]-5-amido-2-indolinone Rf value: 0.45 (silica gel; methylene chloride/methanol=9:1)
$C_{26}H_{21}N_5O_2$
Mass spectrum: m/z=436 (M+H)⁺

(75) 3-Z-[1-(4-((2-diethylamino-ethyl)-aminocarbonyl)-phenyl-amino)-1-phenyl-methylene]-5-amido-2-indolinone-trifluoroacetate Yield: 27% of theory,
Rf value: 0.05 (silica gel; methylene chloride/methanol=9:1)
$C_{29}H_{31}N_5O_3$
Mass spectrum: m/z=497 (M⁺)

(76) 3-Z-[1-(4-acetylaminomethyl-phenylamino)-1-phenyl-methylene]-5-amido-2-indolinone Rf value: 0.4 (silica gel; methylene chloride/methanol=9:1)
$C_{25}H_{22}N_4O_3$
Mass spectrum: m/z=426 (M⁺)

(77) 3-Z-[1-(4-((2-dimethylaminoethyl)-N-methanesulphonyl-amino)-phenylamino)-1-phenyl-methylene]-5-amido-2-indolinone Rf value: 0.1 (silica gel; methylene chloride/methanol=9:1)
Mass spectrum: m/z=519 (M⁺)

(78) 8-Z-[1-(4-(N-(ethoxycarbonylmethyl)-N-methanesulphonyl-amino)-phenylamino)-1-phenyl-methylene]-5-amido-2-indolinone (143) 3-Z-[1-(4-(N-trifluoroethyl-N-(4-chlorophenyl-methyl)-aminomethyl)-phenylamino)-1-phenyl-methylene]-5-amido-2-indolinone

EXAMPLE 5

3-Z-[1-(4-(4-acetyl-piperazinylmethyl)-phenylamino)-1-phenyl-methylene]-5-amido-2-indolinone 25 mg of 3-Z-[1-(4-(4-piperazinylmethyl)-phenylamino)-1-phenyl-methylene]-5-amido-2-indolinone and 0.02 g of triethylamine are dissolved in 10 ml of methylene chloride and mixed with 5 mg of acetyl chloride and the solution is stirred for 16 hours at ambient temperature. Then it is washed with water and the organic phase is then evaporated down.

Yield: 15 mg (68% of theory),
$C_{29}H_{29}N_5O_3$
Mass spectrum: m/z=495 (M⁺)

The following compound is prepared analogously:

(1) 3-Z-[1-(4-(4-benzoyl-piperazinylmethyl)-phenylamino)-1-phenyl-methylene]-5-amido-2-indolinone Prepared from 3-Z-[1-(4-(4-piperazinyl-methyl-phenylamino)-1-phenyl-methylene]-5-amido-2-indolinone and benzoyl chloride.

Yield: 91% of theory,
$C_{34}H_{31}N_5O_3$
Mass spectrum: m/z=557 (M⁺)

EXAMPLE 6

3-Z-[1-(4-diethylcarbamoyl-phenylamino-1-phenyl-methylene]-5-amido-2-indolinone 7 g of resin from step IV are reacted analogously to Example 4 with ethyl 4-aminobenzoate. The moist charged resin is suspended in 30 ml of dioxane and 30 ml of methanol and stirred with 25 ml of 1 N sodium hydroxide solution for 40 hours. Then it is neutralised with dilute hydrochloric acid and washed with methylene chloride, methanol and dimethylformamide. 300 mg of the resin are then suspended in 3 ml of dimethylformamide, and left to stand for 60 hours at ambient temperature with 0.2 ml of diethylamine, 0.5 g of O-(benzotriazol-1-y1)-N,N,N',N'-tetramethyl-uronium-tetrafluoroborate and 0.8 ml of ethyl-diisopropylamine. Finally, the product is cleaved from the resin as described in Example 4.

Yield: 29 mg,
Rf value: 0.46 (silica gel, methylene chloride/methanol 9:1)
$C_{27}H_{26}N_4O_3$
mass spectrum: m/z=454 (M⁺)

The following are prepared analogously:

(1) 3-Z-[1-(4-(piperidinocarbonyl)-phenylamino)-1-phenyl-methylene]-5-amido-2-indolinone Rf value: 0.43 (silica gel; methylene chloride/methanol=9:1)
$C_{28}H_{26}N_4O_3$
mass spectrum: m/z=466 (M⁺)

(2) 3-Z-[1-(4-(4-methylpiperazinocarbonyl)-phenylamino)-1-phenyl-methylene]-5-amido-2-indolinone-trifluoroacetate Rf value: 0.84 (silica gel, methylene chloride/methanol=4:1)
$C_{28}H_{27}N_5O_3$
mass spectrum: m/z=481 (M⁺)

(3) 3-Z-[1-(4-(N-(2-dimethylamino-ethyl)-N-methyl-carbamoyl)-phenylamino)-1-phenyl-methylene]-5-amido-2-indolinone-trifluoroacetate Rf value: 0.25 (silica gel; methylene chloride/methanol=9:1)
$C_{28}H_{29}N_5O_3$
mass spectrum: m/z=484 (M+H)⁺

(4) 3-Z-[1-(4-(N-methoxycarbonylmethyl-carbamoyl)-phenylamino)-1-phenyl-methylene]-5-amido-2-indolinone Rf value: 0.4 (silica gel; methylene chloride/methanol=9:1)
$C_{26}H_{22}N_4O_5$
mass spectrum: m/z=470 (M⁺)

(5) 3-Z-[1-(4-benzylcarbamoyl-phenylamino)-1-phenyl-methylene]-5-amido-2-indolinone Rf value: 0.48 (silica gel; methylene chloride/methanol=9:1)
$C_{30}H_{24}N_4O_3$
mass spectrum: m/z=488 (M⁺)

EXAMPLE 7

3-Z-[1-(4-(N-methyl-benzoylamino)-phenylamino)-1-phenyl-methylene]-5-amido-2-indolinone 4.5 g of resin from step IV are reacted analogously to Example 4 with 3.4 g of 4-(9H-fluoren-9-yl methoxycarbonyl)-methyl-amino)-aniline in dimethylformamide. Then the 9H-fluorene protecting group is cleaved with 4 ml of 30% piperidine in dimethylformamide and the resin is washed several times. 400 mg of the resin are then suspended in 4 ml of dimethylformamide and 0.3 ml of triethylamine and reacted with 0.3 ml of benzoyl chloride for one hour at ambient temperature. Finally the product is cleaved from the resin as described in Example 4.

Yield: 33 mg.

Rf value: 0.45 (silica gel, methylene chloride/methanol= 9:1)

$C_{30}H_{24}N_4O_3$ mass spectrum: m/z=488 (M⁺)

The following are prepared analogously:

(1) 3-Z-[1-(4-(N-methyl-propionylamino)-phenylamino)-1-phenyl-methylene]-5-amido-2-indolinone Rf value: 0.42 (silica gel, methylene chloride/methanol= 9:1)

$C_{26}H_{24}N_4O_3$ mass spectrum: m/z=440 (M⁺)

(2) 3-Z-[1-(4-(N-methyl-butyrylamino)-phenylamino)-1-phenyl-methylene]-5-amido-2-indolinone Rf value: 0.44 (silica gel, methylene chloride/methanol= 9:1)

$C_{27}H_{26}N_4O_3$ mass spectrum: m/z=453 (M–H⁺)

(3) 3-Z-[1-(4-(N-methyl-ethylsulphonylamino)-phenylamino)-1-phenyl-methylene]-5-amido-2-indolinone Rf value: 0.42 (silica gel, methylene chloride/methanol= 9:1)

$C_{25}H_{24}N_4O_4S$ mass spectrum: m/z=475 (M–H⁺)

(4) 3-Z-[1-(4-(N-methyl-propylsulphonylamino)-phenylamino)-1-phenyl-methylene]-5-amido-2-indolinone Rf value: 0.44 (silica gel, methylene chloride/methanol= 9:1)

$C_{25}H_{26}N_4O_4S$ mass spectrum: m/z=491 (M+H)⁺

(5) 3-Z-[1-(4-(N-methyl-phenylsulphonylamino)-phenylamino)-1-phenyl-methylene]-5-amido-2-indolinone Rf value: 0.53 (silica gel, methylene chloride/methanol= 9:1)

$C_{29}H_{24}N_4O_4S$ mass spectrum: m/z=524 (M⁺)

EXAMPLE 8

Dry ampoule containing 75 mg of active substance per 10 ml

| Composition: | |
|---|---|
| Active substance | 75.0 mg |
| Mannitol | 50.0 mg |
| water for injections | ad 10.0 ml |

Preparation:

Active substance and mannitol are dissolved in water. After packaging the solution is freeze-dried. To produce the solution ready for use, the product is dissolved in water for injections.

EXAMPLE 9

Dry ampoule containing 35 mg of active substance per 2 ml

| Composition: | |
|---|---|
| Active substance | 35.0 mg |
| Mannitol | 100.0 mg |
| water for injections | ad 2.0 ml |

Preparation:

Active substance and mannitol are dissolved in water. After packaging, the solution is freeze-dried.

To produce the solution ready for use, the product is dissolved in water for injections.

EXAMPLE 10

Tablet containing 50 mg of active substance

| Composition: | |
|---|---|
| (1) Active substance | 50.0 mg |
| (2) Lactose | 98.0 mg |
| (3) Maize starch | 50.0 mg |
| (4) Polyvinylpyrrolidone | 15.0 mg |
| (5) Magnesium stearate | 2.0 mg |
| | 215.0 mg |

Preparation:

(1), (2) and (3) are mixed together and granulated with an aqueous solution of (4). (5) is added to the dried granulated material. From this mixture tablets are pressed, biplanar, faceted on both sides and with a dividing notch on one side.

Diameter of the tablets: 9 mm.

EXAMPLE 11

Tablet containing 350 mg of active substance

| Preparation: | |
|---|---|
| (1) Active substance | 350.0 mg |
| (2) Lactose | 136.0 mg |
| (3) Maize starch | 80.0 mg |
| (4) Polyvinylpyrrolidone | 30.0 mg |
| (5) Magnesium stearate | 4.0 mg |
| | 600.0 mg |

(1), (2) and (3) are mixed together and granulated with an aqueous solution of (4). (5) is added to the dried granulated material. From this mixture tablets are pressed, biplanar, faceted on both sides and with a dividing notch on one side.

Diameter of the tablets: 12 mm.

EXAMPLE 12

Capsules containing 50 mg of active substance

| Composition: | |
|---|---|
| (1) Active substance | 50.0 mg |
| (2) Dried maize starch | 58.0 mg |
| (3) Powdered lactose | 50.0 mg |
| (4) Magnesium stearate | 2.0 mg |
| | 160.0 mg |

Preparation:

(1) is triturated with (3). This trituration is added to the mixture of (2) and (4) with vigorous mixing.

This powder mixture is packed into size 3 hard gelatin capsules in a capsule filling machine.

EXAMPLE 13

Capsules containing 350 mg of active substance

| Composition: | |
|---|---|
| (1) Active substance | 350.0 mg |
| (2) Dried maize starch | 46.0 mg |
| (3) Powdered lactose | 30.0 mg |
| (4) Magnesium stearate | 4.0 mg |
| | 430.0 mg |

Preparation:

(1) is triturated with (3). This trituration is added to the mixture of (2) and (4) with vigorous mixing.

This powder mixture is packed into size 0 hard gelatin capsules in a capsule filling machine.

EXAMPLE 14

Suppositories containing 100 mg of active substance

| 1 suppository contains: | |
|---|---|
| Active substance | 100.0 mg |
| Polyethyleneglycol (M.W. 1500) | 600.0 mg |
| Polyethyleneglycol (M.W. 6000) | 460.0 mg |
| Polyethylenesorbitan monostearate | 840.0 mg |
| | 2,000.0 mg |

Preparation:

The polyethyleneglycol is melted together with polyethylene sorbitanmonostearate. At 40° C. the ground active substance is homogeneously dispersed in the melt. It is cooled to 38° C. and poured into slightly chilled suppository moulds.

What is claimed is:

1. A compound of the formula I (I)

wherein:

X is an oxygen atom, $R_1$ is a hydrogen atom or a $C_{1-4}$-alkoxycarbonyl group;

$R_2$ is a carboxy, $C_{1-4}$-alkoxycarbonyl, or aminocarbonyl group wherein the amino moiety may be substituted by one or two $C_{1-3}$-alkyl groups and the substituents may be identical or different;

$R_3$ is a phenyl group unsubstituted or substituted by a fluorine, chlorine, or bromine atom, or by a methyl, cyano, or aminomethyl group;

$R_4$ is a hydrogen atom or a $C_{1-4}$-alkyl group; and $R_5$ is a hydrogen atom, a $C_{1-5}$-alkyl group unsubstituted or substituted by a carboxy or $C_{1-3}$-alkoxycarbonyl group, or a benzyl group, a $C_{3-7}$-cycloalkyl group unsubstituted or substituted by a methyl group, an indanyl, pyridyl, oxazolyl, thiazolyl, or imidazolyl group unsubstituted or substituted by a methyl group, to which a phenyl ring may additionally be fused via two adjacent carbon atoms, a methylphenyl group unsubstituted or substituted by a fluorine, chlorine, or bromine atom, or by a methoxy, carboxy, $C_{1-3}$-alkyloxycarbonyl, nitro, or aminosulphonyl group, or a dimethoxyphenyl group, a pyrrolidinyl or piperidinyl group linked via a carbon atom, which may be substituted at the nitrogen atom by a $C_{1-3}$-alkyl group, a phenyl group which is substituted by a trifluoromethoxy group, by a fluorine, chlorine, bromine, or iodine atom, by a $C_{1-3}$-alkoxy group which may be substituted in the 2- or 3-position by an amino, $C_{1-3}$-alkylamino, di-($C_{1-3}$-alkyl)amino, phenyl-$C_{1-3}$-alkylamino, N-($C_{1-3}$-alkyl)-phenyl-$C_{1-3}$-alkylamino, pyrrolidino, or piperidino group, by a phenyl-$C_{1-3}$-alkylamino-$C_{1-3}$-alkyl group which may be in the phenyl nucleus by a fluorine, chlorine, bromine, or iodine atom, by a $C_{1-5}$-alkyl, $C_{1-3}$-alkoxy, or trifluoromethyl group and additionally at the amine nitrogen atom by a $C_{1-3}$-alkyl group wherein the hydrogen atoms from the 2-position may be wholly or partially replaced by fluorine atoms, by a $C_{1-5}$-alkyl, phenyl, imidazolyl, $C_{3-7}$-cycloalkyl, $C_{1-3}$-alkoxy-$C_{1-3}$-alkoxy, phenyl-$C_{1-3}$-alkoxy, carboxy-$C_{1-3}$-alkyl, $C_{1-3}$-alkoxycarbonyl-$C_{1-3}$-alkyl, carboxy, $C_{1-3}$-alkoxycarbonyl, aminocarbonyl, $C_{1-3}$-alkylaminocarbonyl, di-($C_{1-3}$-alkyl)-aminocarbonyl, phenyl-$C_{1-3}$-alkylaminocarbonyl, N-($C_{1-3}$-alkyl)-phenyl-$C_{1-3}$-alkylaminocarbonyl, piperazinocarbonyl, N-($C_{1-3}$-alkyl)-piperazinocarbonyl, nitro, amino, $C_{1-3}$-alkylamino, di-($C_{1-3}$-alkyl)-amino, pyrrolidino, piperidino, morpholino, $C_{2-4}$-alkanoyl-amino, N-($C_{1-3}$-alkyl)-$C_{2-4}$-alkanoylamino, benzoylamino, or N-($C_{1-3}$-alkyl)-benzoylamino group,
by an N-($C_{1-3}$-alkyl)-$C_{2-4}$-alkanoylamino group which is additionally substituted in the alkyl moiety by a carboxy or $C_{1-3}$-alkoxycarbonyl group,
by a $C_{1-3}$-alkylaminocarbonyl or di-($C_{1-3}$-alkyl)-aminocarbonyl group wherein an alkyl moiety is additionally substituted by a di-($C_{1-3}$-alkyl)-amino group, or
by an N-($C_{1-3}$-alkyl)-$C_{1-3}$-alkylsulphonylamino or N-($C_{1-3}$-alkyl)-phenylsulphonylamino group wherein the alkyl moiety may additionally be substituted by a cyano, carboxy, $C_{1-3}$-alkoxycarbonyl, $C_{1-3}$-alkylamino, di-($C_{1-3}$-alkyl)-amino group, aminocarbonyl, $C_{1-3}$-alkylaminocarbonyl, di-($C_{1-3}$-alkyl)-aminocarbonyl, piperidinocarbonyl, or 2-ethylaminocarbonyl group,
a phenyl group unsubstituted or substituted by a $C_{1-3}$-alkyl group wherein the alkyl moiety is substituted by a hydroxy, $C_{1-3}$-alkoxy, carboxy, $C_{1-3}$-alkoxy-carbonyl, amino, $C_{1-5}$-alkylamino, di-($C_{1-5}$-alkyl)-amino, $C_{2-4}$-alkanoylamino, N-($C_{1-3}$-alkyl)-$C_{2-4}$-alkanoylamino, pyrrolidino, dehydropyrrolidino, piperidino, dehydropiperidino, 3-hydroxypiperidino, 4-hydroxypiperidino, hexamethyleneimino, morpholino, thiomorpholino, piperazino, 4-($C_{1-3}$-alkyl)-piperazino, 4-phenyl-piperazino, 4-($C_{2-4}$-alkanoyl)-piperazino, 4-benzoyl-piperazino, or imidazolyl group, wherein the abovementioned saturated cycloalkyleneimino rings, $C_{1-5}$-alkylamino or di-($C_{1-5}$-alkyl)-amino groups may additionally be substituted by one or two $C_{1-5}$-alkyl groups, by a $C_{3-7}$-cycloalkyl, hydroxy, $C_{1-3}$-alkoxy, carboxy, $C_{1-3}$-alkoxycarbonyl, aminocarbonyl, $C_{1-3}$-alkylaminocarbonyl, or di-($C_{1-3}$-alkyl)-aminocarbonyl group, by a phenyl-$C_{1-3}$-alkyl or phenyl group optionally mono- or disubstituted in the phenyl nucleus by fluorine, chlorine, bromine, or iodine atoms or by $C_{1-3}$-alkyl or cyano groups, wherein the substituents may be identical or different, or a methylene group adjacent to the nitrogen atom in the abovementioned cycloalkyleneimino rings may be replaced by a carbonyl or sulphonyl group, and the abovementioned monosubstituted phenyl groups may additionally be substituted by a fluorine, chlorine, or bromine atom or by a methyl, amino, $C_{1-3}$-alkylamino, or di-($C_{1-3}$-alkyl)-amino group, or a phenyl ring unsubstituted or substituted by one or two $C_{1-3}$-alkoxy groups may be fused to one of the abovementioned unsubstituted cycloalkyleneimino rings via two adjacent carbon atoms, or a salt thereof.

2. The compound of the formula I, according to claim 1, wherein:
X is an oxygen atom;
$R_1$ is a hydrogen atom;
$R_2$ is a carboxy, $C_{1-4}$-alkoxycarbonyl or aminocarbonyl group wherein the amino moiety may be substituted by one or two $C_{1-3}$-alkyl groups and the substituents may be identical or different;
$R_3$ is a phenyl group unsubstituted or substituted by a methyl group;
$R_4$ is a hydrogen atom or a methyl group, and
$R_5$ is a hydrogen atom,
a $C_{1-3}$-alkyl group, a benzyl groups or a methyl or ethyl group substituted by a carboxy or $C_{1-3}$-alkoxycarbonyl group,
a $C_{3-7}$-cycloalkyl group unsubstituted or substituted by a methyl group,
an indanyl, pyridyl, oxazolyl, thiazolyl, or imidazolyl group unsubstituted or substituted by a methyl group, to which a phenyl ring may additionally be fused via two adjacent carbon atoms,
a methylphenyl group unsubstituted or substituted by a fluorine, chlorine, or bromine atom, or by a methoxy, carboxy, $C_{1-3}$-alkyloxycarbonyl, nitro, or aminosulphonyl group, or a dimethoxyphenyl group,
a 3-pyrrolidinyl or 4-piperidinyl group which may be substituted at the nitrogen atom by a $C_{1-3}$-alkyl group,
a phenyl group which is substituted by a trifluoromethoxy, benzyloxy, cyano, or nitro group, by a fluorine, chlorine, bromine, or iodine atom,
by a $C_{1-3}$-alkoxy group, wherein the ethoxy and n-propoxy groups may each be terminally substituted by a dimethylamino, diethylamino, N-ethyl-methylamino, N-benzyl-methylamino, or piperidino group,
by a phenyl-$C_{1-3}$-alkylamino-$C_{1-3}$-alkyl group which may be substituted in the phenyl nucleus by a fluorine, chlorine, bromine, or iodine atom, by a methyl, methoxy or trifluoromethyl group and additionally at the amine nitrogen atom by a $C_{1-5}$-alkyl or 2,2,2-trifluoroethyl group,
by a $C_{1-4}$-alkyl, phenyl, imidazolyl, cyclohexyl, methoxymethyl, carboxymethyl, $C_{1-3}$-alkoxycarbonyl-methyl, carboxy, $C_{1-3}$-alkoxycarbonyl, aminocarbonyl, $C_{1-3}$-alkylaminocarbonyl, di-($C_{1-3}$-alkyl)-aminocarbonyl, phenyl-$C_{1-3}$-alkylaminocarbonyl, N-($C_{1-3}$-alkyl)-phenyl-$C_{1-3}$-alkylaminocarbonyl, piperazinocarbonyl, N-($C_{1-3}$-alkyl)-piperazinocarbonyl, amino, $C_{1-3}$-alkylamino, di-($C_{1-3}$-alkyl)-amino, pyrrolidino, piperidino, morpholino, $C_{2-4}$-alkanoyl-amino, N-($C_{1-3}$-alkyl)-$C_{2-4}$-alkanoylamino, benzoylamino, or N-($C_{1-3}$alkyl)-benzoylamino group,
by an N-($C_{1-3}$-alkyl)-$C_{2-4}$-alkanoylamino group which is additionally substituted in the alkyl moiety by a carboxy or $C_{1-3}$-alkoxycarbonyl group,
by a $C_{1-3}$-alkylaminocarbonyl or di-($C_{1-3}$-alkyl)-aminocarbonyl group wherein an alkyl moiety is additionally substituted by a di-($C_{1-3}$-alkyl)-amino group, or by an N-($C_{1-3}$-alkyl)-$C_{1-3}$-alkylsulphonylamino or N-($C_{1-3}$-alkyl)-phenylsulphonylamino group wherein the alkyl moiety may additionally be substituted by a cyano, carboxy, $C_{1-3}$-alkoxycarbonyl, $C_{1-3}$-alkylamino, di-($C_{1-3}$-alkyl)-amino group, aminocarbonyl, $C_{1-3}$-alkylaminocarbonyl, di-($C_{1-3}$-alkyl)-aminocarbonyl, piperidinocarbonyl, or 2-ethylaminocarbonyl group, a phenyl group unsubstituted or substituted by a $C_{1-3}$-alkyl group wherein the alkyl moiety is substituted by a hydroxy, $C_{1-3}$-alkoxy, carboxy, $C_{1-3}$-alkoxy-carbonyl, amino, $C_{1-5}$-alkylamino, di-($C_{1-5}$-alkyl)-amino, $C_{2-4}$-alkanoylamino, N-($C_{1-3}$-alkyl)-$C_{2-4}$-alkanoylamino, pyrrolidino, dehydropyrrolidino, piperidino, dehydropiperidino, 4-hydroxypiperidino, hexamethyleneimino, morpholino, thiomorpholino, piperazino, 4-($C_{1-3}$-alkyl)-piperazino, 4-phenyl-piperazino, 4-($C_{2-4}$-alkanoyl)-piperazino, 4-benzoyl-piperazino, or imidazolyl group, wherein the abovementioned saturated cycloalkyleneimino rings may additionally be substituted by a phenyl group or by one or two methyl groups, the abovementioned $C_{1-5}$-alkylamino and di-($C_{1-5}$-alkyl)-amino groups may additionally be substituted by one or two $C_{1-3}$-alkyl groups, by a cyclohexyl, hydroxy, $C_{1-3}$-alkoxy, carboxy, $C_{1-3}$-alkoxycarbonyl, aminocarbonyl, $C_{1-3}$-alkylaminocarbonyl or di-($C_{1-3}$-alkyl)-aminocarbonyl group, by a phenyl-$C_{1-3}$-alkyl or phenyl group unsubstituted or substituted in the phenyl nucleus by a fluorine, chlorine, bromine, or iodine atom or by a methyl or cyano group, or a methylene group adjacent to the nitrogen atom in the abovementioned cycloalkyleneimino rings may be replaced by a carbonyl or sulphonyl group, and the abovementioned monosubstituted phenyl groups may additionally be substituted by a fluorine, chlorine, or bromine atom or by a methyl, amino, $C_{1-3}$-alkylamino, or di-($C_{1-3}$-alkyl)-amino group, or a phenyl ring unsubstituted or substituted by one or two $C_{1-3}$-alkoxy groups may be fused to one of the abovementioned unsubstituted cycloalkyleneimino rings via two adjacent carbon atoms, or a salt thereof.

3. The compound of the formula I, according to claim 1 wherein;

X is an oxygen atom;

$R_1$ is a hydrogen atom;

$R_2$ is a carboxy or aminocarbonyl group wherein the amino moiety may be substituted by one or two $C_{1-3}$-alkyl groups and the substituents may be identical or different;

$R_3$ is a phenyl group unsubstituted or substituted by a methyl group;

$R_4$ is a hydrogen atom; and $R_5$ is a hydrogen atom, a 3-pyrrolidinyl or 4-piperidinyl group which may be substituted at the nitrogen atom by a $C_{1-3}$-alkyl group, a phenyl group which is substituted by a $C_{1-3}$-alkoxy group, wherein the ethoxy and n-propoxy groups may each be terminally substituted by a dimethylamino, diethylamino, N-ethyl-methylamino, N-benzyl-methylamino, or piperidino group, by a phenyl-$C_{1-3}$-alkylamino-$C_{1-3}$-alkyl group which may be substituted in the phenyl nucleus by a fluorine, chlorine, bromine, or iodine atom, by a methyl, methoxy, or trifluoromethyl group and additionally at the amine nitrogen atom by a $C_{1-5}$-alkyl or 2,2,2-trifluoroethyl group, a phenyl group unsubstituted or substituted by a $C_{1-3}$-alkyl group wherein the alkyl moiety is substituted by a hydroxy, $C_{1-3}$-alkoxy, carboxy, $C_{1-3}$-alkoxy-carbonyl, amino, $C_{1-5}$-alkylamino, di-($C_{1-5}$-alkyl)-amino, $C_{2-4}$-alkanoylamino, N-($C_{1-3}$-alkyl)-$C_{2-4}$-alkanoylamino, pyrrolidino, dehydropyrrolidino, piperidino, dehydropiperidino, 4-hydroxypiperidino, hexamethyleneimino, morpholino, thiomorpholino, piperazino, 4-($C_{1-3}$-alkyl)-piperazino, 4-phenyl-piperazino, 4-($C_{2-4}$-alcanoyl)-piperazino, 4-benzoyl-piperazino, or imidazolyl group, wherein the abovementioned saturated cycloalkyleneimino rings may additionally be substituted by a phenyl group or by one or two methyl groups, the abovementioned $C_{1-5}$-alkylamino and di-($C_{1-5}$-alkyl)-amino groups may additionally be substituted by one or two $C_{1-3}$-alkyl groups, by a cyclohexyl, hydroxy, $C_{1-3}$-alkoxy, carboxy, $C_{1-3}$-alkoxycarbonyl, aminocarbonyl, $C_{1-3}$-alkylarninocarbonyl, or di-($C_{1-3}$-alkyl)-aminocarbonyl group, by a phenyl-$C_{1-3}$-alkyl or phenyl group unsubstituted or substituted in the phenyl nucleus by a fluorine, chlorine, bromine, or iodine atom or by a methyl or cyano group, or a methylene group adjacent to the nitrogen atom in the abovementioned cycloalkyleneimino rings may be replaced by a carbonyl or sulphonyl group, and the abovementioned monosubstituted phenyl groups may additionally be substituted by a fluorine, chlorine, or bromine atom or by a methyl, amino, $C_{1-3}$-alkylamino, or di-($C_{1-3}$-alkyl)-amino group, or a phenyl ring unsubstituted or substituted by one or two $C_{1-3}$-alkoxy groups may be fused to one of the abovementioned unsubstituted cycloalkylencimino rings via two adjacent carbon atoms, or a salt thereof.

4. The compound of the formula I, according to claim 1, wherein the group $R_2$ is in the 5-position.

5. A compound selected from the group consisting of:
   (a) 3-Z-[1-(4-aminomethyl-phenylamino)-1-phenyl-methylene]-5-amido-2-indolinone;
   (b) 3-Z-(1-phenylamino)-1-phenyl-methylene)-5-amido-2-indolinone;
   (c) 3-Z-[1-(4-bromophenylamino)-1-phenyl-methylene]-5-amido-2-indolinone;
   (d) 3-Z-[1-(4-dimethylamino-methyl)-phenylamino)-1-phenyl-methylene]-5-amido-2-indolinone;
   (e) 3-Z-[1-(4-pyrrolidinomethyl-phenylamino)-1-phenyl-methylene]-5-amido-2-indolinone;
   (f) 3-Z-[1-(4-piperidinomethyl-phenylamino)-1-phenyl-methylene]-5-amido-2-indolinone;
   (g) 3-Z-[1-(4-hexamethyleneiminomethyl-phenylamino)-1-phenyl-methylene]-5-amido-2-indolinone;
   (h) 3-Z-[1-(4-(4-benzyl-pipcridino)-methyl)-phenylamino)-1-phenyl-methylene]-5-amido-2-indolinone;
   (i) 3-Z-[1-(4-(N-butyl-aminomethyl)-phenylamino)-1-phenyl-methylene]-5-amido-2-indolinone;
   (j) 3-Z-[1-(4-(N-(phenyl-methyl)-aminomethyl)-phenylamino)-1-phenyl-methylene]-5-amido-2-indolinone;
   (k) 3-Z-[1-(4-(N-methyl-N-benzyl-amino-methyl)-phenylamino)-1-phenyl-methylene]-5-amido-2-indolinone;
   (l) 3-Z-[1-(4-piperidino-methyl-phenylamino)-1-phenyl-methylene]-5-dimethylcarbamoyl-2-indolinone;
   (m) 3-Z-[1-(4-piperidino-methyl-phenylamino)-1-phenyl-methylene]-5-diethylcarbamoyl-2-indolinone;
   (n) 3-Z-[1-(4-(3-diethylamino-propoxy)-phenylamino)-1-phenyl-methylene]-5-amido-2-indolinone, or a salt thereof.

6. A pharmaceutical composition comprising a compound of the formula I, according to claim 1, or a pharmaceutically acceptable salt thereof.

7. A method for treating excessive or abnormal cell proliferation which comprises administering an effective amount of the compound of one of claims 1, 2, 3, 4, or 5.

* * * * *